United States Patent
Mauldin et al.

(10) Patent No.: US 9,044,321 B2
(45) Date of Patent: Jun. 2, 2015

(54) INTEGRATED IMPLANT

(71) Applicant: SI-Bone Inc., San Jose, CA (US)

(72) Inventors: Richard G. Mauldin, Erie, CO (US); Mark A. Reiley, Washington, DC (US)

(73) Assignee: SI-Bone Inc., San Jose, CA (US)

( * ) Notice: Subject to any disclaimer, the term of this patent is extended or adjusted under 35 U.S.C. 154(b) by 0 days.

(21) Appl. No.: 13/791,746

(22) Filed: Mar. 8, 2013

(65) Prior Publication Data

US 2013/0238093 A1    Sep. 12, 2013

Related U.S. Application Data

(60) Provisional application No. 61/609,221, filed on Mar. 9, 2012.

(51) Int. Cl.
*A61F 2/28*    (2006.01)
*A61B 17/16*   (2006.01)
*A61B 17/84*   (2006.01)

(52) U.S. Cl.
CPC . *A61F 2/28* (2013.01); *A61B 17/16* (2013.01); *A61B 17/846* (2013.01)

(58) Field of Classification Search
CPC .............. A61F 2/28; A61F 2/44; A61B 17/16
USPC .......... 623/20.11, 23.47–23.64, 23.75, 23.76, 623/17.11–17.16; 606/95–104, 246, 279
See application file for complete search history.

(56) References Cited

U.S. PATENT DOCUMENTS

| | | |
|---|---|---|
| 1,951,278 A | 3/1934 | Ericsson |
| 2,136,471 A | 11/1938 | Schneider |
| 2,243,717 A | 5/1941 | Moreira |
| 2,414,882 A | 7/1947 | Longfellow |
| 2,675,801 A | 4/1954 | Bambara et al. |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 4,156,943 A | 6/1979 | Collier |
| 4,341,206 A | 7/1982 | Perrett et al. |
| 4,344,190 A | 8/1982 | Lee et al. |

(Continued)

FOREIGN PATENT DOCUMENTS

| | | |
|---|---|---|
| EP | 1287796 A1 | 3/2003 |
| JP | 05-176942 A | 7/1993 |

(Continued)

OTHER PUBLICATIONS

Mauldin et al.; U.S. Appl. No. 13/888,249 entitled "Fenestrated Implant," filed May 6, 2013.

(Continued)

*Primary Examiner* — Yashita Sharma

(74) *Attorney, Agent, or Firm* — Shay Glenn LLP

(57) ABSTRACT

An implant having an integrated cutting broach and/or cutting burr. The integrated implant may be inserted without requiring separate steps for drilling and broaching bone. The integrated implant assembly may include an integrated implant, a flexible sheath, a delivery rod, and a delivery pin. The implant may have a core which may have any of a variety of cross-sectional geometries. A method for fusing bone may involve inserting the implant laterally through the ilium, through the sacral-iliac joint, and into the sacrum.

11 Claims, 15 Drawing Sheets

(56) References Cited

U.S. PATENT DOCUMENTS

| | | |
|---|---|---|
| 4,399,813 A | 8/1983 | Barber |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,981,481 A | 1/1991 | Kranz et al. |
| 5,034,011 A | 7/1991 | Howland |
| 5,035,697 A | 7/1991 | Frigg |
| 5,041,118 A | 8/1991 | Wasilewski |
| 5,053,035 A | 10/1991 | McClaren |
| 5,066,296 A | 11/1991 | Chapman et al. |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,433,718 A | 7/1995 | Brinker |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,609,636 A | 3/1997 | Kohrs et al. |
| 5,626,616 A | 5/1997 | Speece |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,743,912 A | 4/1998 | LaHille et al. |
| 5,759,035 A | 6/1998 | Ricci |
| 5,766,174 A | 6/1998 | Perry |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,928,239 A | 7/1999 | Mirza |
| 5,941,885 A | 8/1999 | Jackson |
| 5,961,554 A | 10/1999 | Janson et al. |
| 6,010,507 A | 1/2000 | Rudloff |
| 6,015,409 A | 1/2000 | Jackson |
| 6,053,916 A | 4/2000 | Moore |
| 6,056,749 A | 5/2000 | Kuslich |
| 6,086,589 A | 7/2000 | Kuslich et al. |
| 6,096,080 A | 8/2000 | Nicholson et al. |
| 6,120,504 A | 9/2000 | Brumback et al. |
| 6,143,031 A * | 11/2000 | Knothe et al. ............. 623/17.16 |
| 6,197,062 B1 | 3/2001 | Fenlin |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 | 10/2001 | Michelson |
| 6,306,140 B1 | 10/2001 | Siddiqui |
| 6,319,253 B1 | 11/2001 | Ackeret et al. |
| 6,409,768 B1 | 6/2002 | Tepic et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 | 3/2003 | Warburton |
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,723,099 B1 | 4/2004 | Goshert |
| 6,740,118 B2 | 5/2004 | Eisermann et al. |
| 6,743,257 B2 | 6/2004 | Castro |
| 6,793,656 B1 | 9/2004 | Mathews |
| 6,984,235 B2 | 1/2006 | Huebner |
| 7,118,579 B2 | 10/2006 | Michelson |
| 7,175,663 B2 | 2/2007 | Stone |
| 7,211,085 B2 | 5/2007 | Michelson |
| 7,223,269 B2 | 5/2007 | Chappuis |
| 7,335,205 B2 | 2/2008 | Aeschlimann et al. |
| 7,338,500 B2 | 3/2008 | Chappuis |
| 7,452,359 B1 | 11/2008 | Michelson |
| 7,452,369 B2 | 11/2008 | Barry |
| 7,481,831 B2 | 1/2009 | Bonutti |
| 7,534,254 B1 | 5/2009 | Michelson |
| 7,569,054 B2 | 8/2009 | Michelson |
| 7,601,155 B2 | 10/2009 | Petersen |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,850,732 B2 | 12/2010 | Heinz |
| 7,857,832 B2 | 12/2010 | Culbert et al. |
| 7,887,565 B2 | 2/2011 | Michelson |
| 7,909,832 B2 | 3/2011 | Michelson |
| 7,922,765 B2 | 4/2011 | Reiley |
| 7,942,879 B2 | 5/2011 | Christie et al. |
| 8,066,705 B2 | 11/2011 | Michelson |
| 8,066,709 B2 | 11/2011 | Michelson |
| 8,142,481 B2 | 3/2012 | Warnick |
| 8,202,305 B2 | 6/2012 | Reiley |
| 8,308,779 B2 | 11/2012 | Reiley |
| 8,348,950 B2 | 1/2013 | Assell et al. |
| 8,388,667 B2 | 3/2013 | Reiley et al. |
| 8,394,129 B2 | 3/2013 | Morgenstern Lopez |
| 8,398,635 B2 | 3/2013 | Vaidya |
| 8,414,648 B2 | 4/2013 | Reiley |
| 8,425,570 B2 | 4/2013 | Reiley |
| 8,444,693 B2 | 5/2013 | Reiley |

(56) References Cited

U.S. PATENT DOCUMENTS

| | | |
|---|---|---|
| 8,470,004 B2 | 6/2013 | Reiley |
| 8,608,802 B2 | 12/2013 | Bagga et al. |
| D697,209 S | 1/2014 | Walthall et al. |
| 8,641,737 B2 | 2/2014 | Matthis et al. |
| 8,672,986 B2 | 3/2014 | Klaue et al. |
| 8,840,623 B2 | 9/2014 | Reiley |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0038123 A1 | 3/2002 | Visotsky et al. |
| 2002/0049497 A1 | 4/2002 | Mason |
| 2002/0120275 A1 | 8/2002 | Schmieding et al. |
| 2002/0128652 A1 | 9/2002 | Ferree |
| 2002/0143335 A1 | 10/2002 | von Hoffmann et al. |
| 2002/0151903 A1 | 10/2002 | Takei et al. |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083688 A1 | 5/2003 | Simonson |
| 2003/0097131 A1 | 5/2003 | Schon et al. |
| 2003/0139815 A1 | 7/2003 | Grooms et al. |
| 2003/0199983 A1 | 10/2003 | Michelson |
| 2003/0233147 A1 | 12/2003 | Nicholson et al. |
| 2004/0024458 A1 | 2/2004 | Senegas et al. |
| 2004/0073216 A1 | 4/2004 | Lieberman |
| 2004/0073314 A1 | 4/2004 | White et al. |
| 2004/0087948 A1 | 5/2004 | Suddaby |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0147929 A1 | 7/2004 | Biedermann et al. |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0210221 A1 | 10/2004 | Kozak et al. |
| 2004/0225360 A1 | 11/2004 | Malone |
| 2005/0015059 A1 | 1/2005 | Sweeney |
| 2005/0033435 A1 | 2/2005 | Belliard et al. |
| 2005/0049590 A1 | 3/2005 | Alleyne et al. |
| 2005/0055023 A1 | 3/2005 | Sohngen et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0124993 A1 | 6/2005 | Chappuis |
| 2005/0137605 A1 | 6/2005 | Assell et al. |
| 2005/0159749 A1 | 7/2005 | Levy et al. |
| 2005/0165398 A1 | 7/2005 | Reiley |
| 2005/0192572 A1 | 9/2005 | Abdelgany et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2006/0036247 A1 | 2/2006 | Michelson |
| 2006/0036251 A1 | 2/2006 | Reiley |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089656 A1 | 4/2006 | Allard et al. |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0217717 A1 | 9/2006 | Whipple |
| 2006/0241776 A1 | 10/2006 | Brown et al. |
| 2006/0293662 A1 | 12/2006 | Boyer, II et al. |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1* | 4/2007 | Bonutti et al. .................. 606/99 |
| 2007/0093841 A1 | 4/2007 | Hoogland |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161989 A1 | 7/2007 | Heinz et al. |
| 2007/0233146 A1 | 10/2007 | Henniges et al. |
| 2007/0250166 A1 | 10/2007 | McKay |
| 2007/0270879 A1 | 11/2007 | Isaza et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0065093 A1 | 3/2008 | Assell et al. |
| 2008/0065215 A1 | 3/2008 | Reiley |
| 2008/0109083 A1 | 5/2008 | Van Hoeck et al. |
| 2008/0154374 A1 | 6/2008 | Labrom |
| 2008/0161810 A1 | 7/2008 | Melkent |
| 2008/0234758 A1 | 9/2008 | Fisher et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0306554 A1 | 12/2008 | McKinley |
| 2009/0018660 A1 | 1/2009 | Roush |
| 2009/0024174 A1 | 1/2009 | Stark |
| 2009/0036927 A1 | 2/2009 | Vestgaarden |
| 2009/0043393 A1 | 2/2009 | Duggal et al. |
| 2009/0099602 A1 | 4/2009 | Aflatoon |
| 2009/0099610 A1 | 4/2009 | Johnson et al. |
| 2009/0105770 A1 | 4/2009 | Berrevooets et al. |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0187247 A1 | 7/2009 | Metcalf, Jr. et al. |
| 2009/0216238 A1 | 8/2009 | Stark |
| 2009/0259261 A1 | 10/2009 | Reiley |
| 2009/0270929 A1 | 10/2009 | Suddaby |
| 2009/0287254 A1 | 11/2009 | Nayet et al. |
| 2009/0312798 A1 | 12/2009 | Varela |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0145461 A1 | 6/2010 | Landry et al. |
| 2010/0160977 A1 | 6/2010 | Gephart et al. |
| 2010/0191292 A1 | 7/2010 | DeMeo et al. |
| 2010/0268228 A1 | 10/2010 | Petersen |
| 2010/0280622 A1 | 11/2010 | McKinley |
| 2010/0286778 A1 | 11/2010 | Eisermann et al. |
| 2010/0331893 A1 | 12/2010 | Geist et al. |
| 2011/0009869 A1 | 1/2011 | Marino et al. |
| 2011/0022089 A1 | 1/2011 | Assell et al. |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0087294 A1 | 4/2011 | Reiley |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0118796 A1 | 5/2011 | Reiley et al. |
| 2011/0153018 A1 | 6/2011 | Walters et al. |
| 2011/0184478 A1 | 7/2011 | Reiley |

(56) References Cited

U.S. PATENT DOCUMENTS

| | | |
|---|---|---|
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0230966 A1 | 9/2011 | Trieu |
| 2011/0238181 A1 | 9/2011 | Trieu |
| 2011/0257755 A1 | 10/2011 | Bellemere et al. |
| 2011/0264229 A1 | 10/2011 | Donner |
| 2011/0295272 A1 | 12/2011 | Assell et al. |
| 2012/0095560 A1 | 4/2012 | Donner |
| 2012/0179256 A1 | 7/2012 | Reiley |
| 2012/0191191 A1 | 7/2012 | Trieu |
| 2012/0253398 A1 | 10/2012 | Metcalf et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0085535 A1 | 4/2013 | Greenhalgh et al. |
| 2013/0123850 A1 | 5/2013 | Schoenefeld et al. |
| 2013/0131739 A1 | 5/2013 | Reiley |
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0231746 A1 | 9/2013 | Ginn et al. |
| 2013/0245703 A1 | 9/2013 | Warren et al. |
| 2013/0253654 A1 | 9/2013 | Reiley |
| 2014/0012340 A1 | 1/2014 | Beck et al. |
| 2014/0031934 A1 | 1/2014 | Trieu |
| 2014/0031935 A1 | 1/2014 | Donner et al. |
| 2014/0046380 A1 | 2/2014 | Asfora |
| 2014/0088596 A1 | 3/2014 | Assell et al. |
| 2014/0088707 A1 | 3/2014 | Donner et al. |
| 2014/0142700 A1 | 5/2014 | Donner et al. |
| 2014/0200618 A1 | 7/2014 | Donner et al. |
| 2014/0207240 A1 | 7/2014 | Stoffman et al. |
| 2014/0222150 A1 | 8/2014 | Reiley |
| 2014/0249589 A1 | 9/2014 | Reiley et al. |
| 2014/0257298 A1 | 9/2014 | Reiley |
| 2014/0257408 A1 | 9/2014 | Trieu et al. |
| 2014/0257415 A1 | 9/2014 | Reiley |
| 2014/0276846 A1 | 9/2014 | Mauldin et al. |
| 2014/0276851 A1 | 9/2014 | Schneider et al. |
| 2014/0277462 A1 | 9/2014 | Yerby et al. |
| 2014/0277463 A1 | 9/2014 | Yerby et al. |
| 2014/0288605 A1 | 9/2014 | Mesiwala et al. |
| 2014/0364917 A1 | 12/2014 | Sandstrom et al. |

FOREIGN PATENT DOCUMENTS

| | | |
|---|---|---|
| JP | 2004121841 | 4/2004 |
| JP | 2004512895 | 4/2004 |
| JP | 2004516866 | 6/2004 |
| JP | 2006506181 | 2/2006 |
| WO | WO97/31517 A2 | 8/1997 |
| WO | WO02/38054 | 5/2002 |
| WO | WO 03/007839 A2 | 1/2003 |
| WO | WO2004/002344 | 1/2004 |
| WO | WO2006003316 | 1/2006 |
| WO | WO2010/105196 A1 | 9/2010 |
| WO | WO 2011/110865 A2 | 9/2011 |
| WO | WO 2013/000071 A1 | 1/2013 |

OTHER PUBLICATIONS

Reiley, Mark; U.S. Appl. No. 13/925,678 entitled "Apparatus, systems, and methods for stabilizing a spondylolisthesis" filed Jun. 24, 2013.

Al-Khayer et al.; Percutaneous sacroiliac joint arthrodesis, a novel technique; J Spinal Disord Tech; vol. 21; No. 5; pp. 359-363; Jul. 2008.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Wise et al.; Minimally invasive sacroiliac arthrodesis, outcomes of a new technique; J Spinal Disord Tech; vol. 21; No. 8; pp. 579-584; Dec. 2008.

Reiley, Mark A.; U.S. Appl. No. 12/357,483 entitled "Systems and methods for the fixation or fusion of bone in the hand and wrist," filed Jan. 22, 2009 (abandoned).

Reiley et al.; U.S. Appl. No. 13/786,037 entitled "Systems and methods for the fixation or fusion of bone using compressive implants," filed Mar. 5, 2013.

Mauldin, R. G.; U.S. Appl. No. 13/791,801 entitled "Threaded implant," filed Mar. 8, 2013.

Mauldin, R. G.; U.S. Appl. No. 13/791,837 entitled "Artificial joint," filed Mar. 8, 2013.

Mauldin, R. G.; U.S. Appl. No. 13/791,849 entitled "Revision tool and method," filed Mar. 8, 2013.

Mauldin et al.; U.S. Appl. No. 13/794,542 entitled "Tissue dilator and protector," filed Mar. 11, 2013.

Mauldin et al.; U.S. Appl. No. 13/794,580 entitled "Guide pin," filed Mar. 11, 2013.

Mauldin et al.; U.S. Appl. No. 13/794,611 entitled "Impactor," filed Mar. 11, 2013.

Reiley, Mark.; U.S. Appl. No. 13/858,814 entitled "Apparatus, systems, and methods for achieving trans-iliac lumbar fusion," filed Apr. 8, 2013.

Reiley, Mark; U.S. Appl. No. 13/867,941 entitled "Apparatus, systems, and methods for achieving anterior lumbar interbody fusion," filed Apr. 22, 2013.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Reckling et al.; U.S. Appl. No. 14/515,416 entitled "Implant Placement," filed Oct. 15, 2014.

Acumed; Acutrak Headless Compressioin Screw (product information); 12 pgs; © 2005; retrieved Sep. 25, 2014 from http://www.rcsed.ac.uk/fellows/Ivanrensburg/classification/surgtech/acumed/manuals/acutrak-brochure%200311.pdf.

Reiley; U.S. Appl. No. 14/488,144 entitled "Systems and methods for the fixation of bone," filed Sep. 16, 2014.

Mauldin, Richard; U.S. Appl. No. 14/332,294 entitled "Artificial SI Joint," filed Jul. 15, 2014.

\* cited by examiner

*(Anterior)*

*(Posterior)*

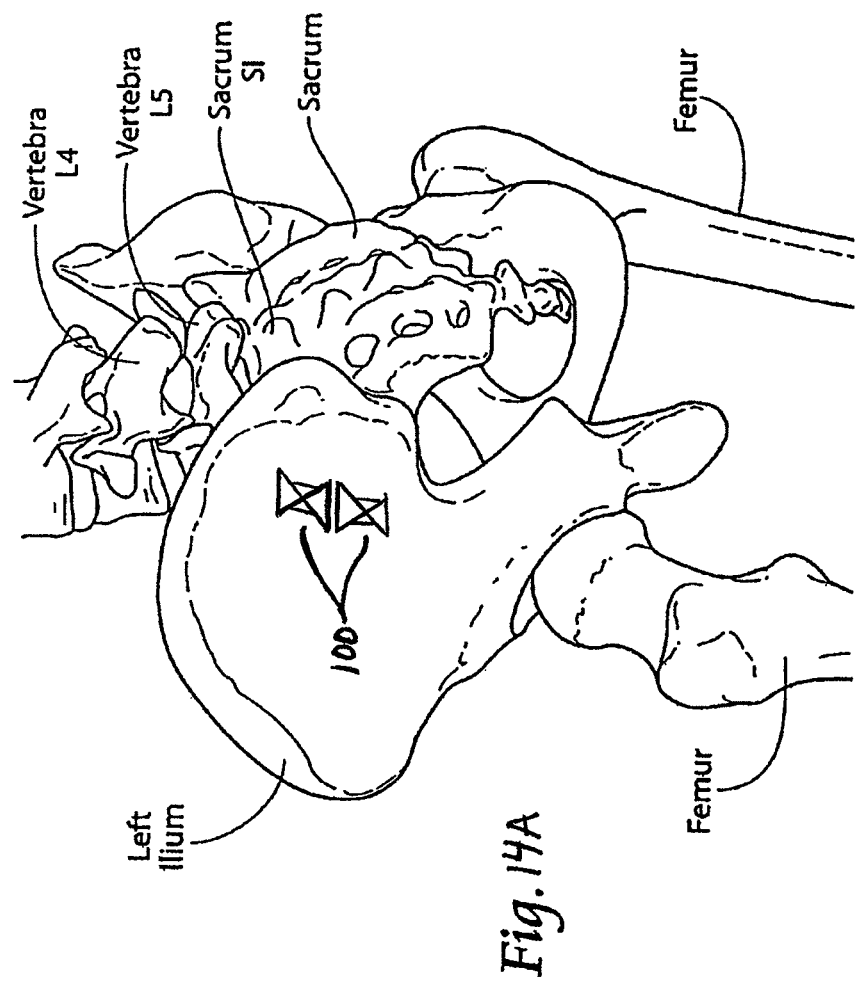

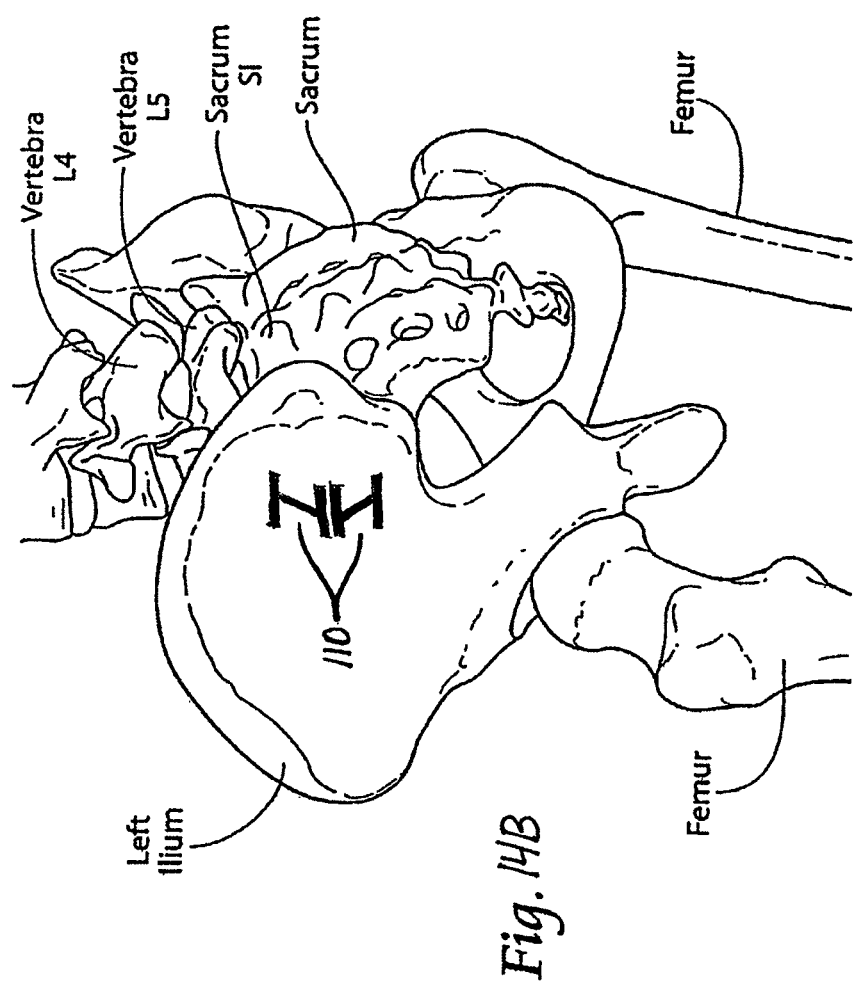

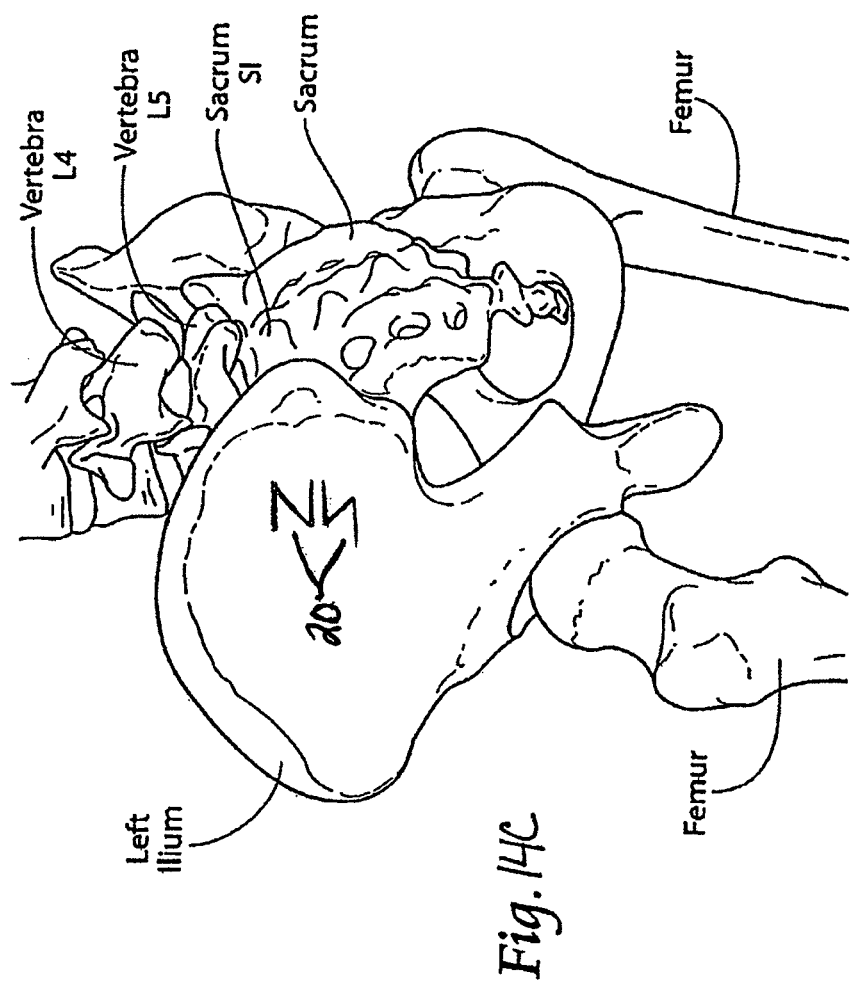

INTEGRATED IMPLANT

CROSS REFERENCE TO RELATED APPLICATIONS

This patent application claims priority to U.S. Provisional Application No. 61/609,221, titled "INTEGRATED IMPLANT", filed on Mar. 9, 2012. This patent application may be related to one or more of the following patent applications: U.S. Patent Publication No. 2011/0087294, titled "SYSTEMS AND METHODS FOR THE FUSION OF THE SACRAL-ILIAC JOINT", filed on Oct. 5, 2010 and U.S. Patent Publication No. 2011/0118785, titled "APPARATUS, SYSTEMS, AND METHODS FOR ACHIEVING ANTERIOR LUMBAR INTERBODY FUSION", filed on Dec. 6, 2010. Each of these references is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention generally relates to the fixation or fusion of bone.

BACKGROUND

Many types of hardware are available both for the fixation of bones that are fractured and for the fixation of bones that are to be fused. A fusion is an operation where two bones, usually separated by a joint, are allowed to grow together into one bone. The medical term for this type of fusion procedure is arthrodesis.

For example, lumbar fusion procedures have been used in the treatment of pain and the effects of degenerative changes in the lower back. An example of a lumbar fusion is a fusion in the S1-L5-L4 region in the spine.

Another example, the human hip girdle (see FIGS. 9 and 10) is made up of three large bones joined by two relatively immobile joints. One of the bones is called the sacrum and it lies at the bottom of the lumbar spine, where it connects with the L5 vertebra. The other two bones are commonly called "hip bones" and are technically referred to as the right ilium and the left ilium. The sacrum connects with both hip bones at the left and right sacroiliac joints (in shorthand, the SI-Joint).

The SI-Joint functions in the transmission of forces from the spine to the lower extremities, and vice-versa. The SI-Joint has been described as a pain generator for up to 22% of lower back pain.

To relieve pain generated from the SI Joint, sacroiliac joint fusion is typically indicated as a surgical treatment, e.g., for degenerative sacroiliitis, inflammatory sacroiliitis, iatrogenic instability of the sacroiliac joint, osteitis condensans ilii, or traumatic fracture dislocation of the pelvis. Currently, screws and screws with plates are used for sacro-iliac fusion. At the same time the cartilage has to be removed from the "synovial joint" portion of the SI joint. This requires a large incision to approach the damaged, subluxed, dislocated, fractured, or degenerative joint.

There is a need for improved bone fusion treatments for addressing chronic hip, joint or back pain.

SUMMARY OF THE DISCLOSURE

The present invention relates to the fixation or fusion of bone.

Some embodiments provide for an integrated implant delivery assembly having an integrated bone fusion implant having a core and a cutting broach at a distal end of the core; a delivery rod; a delivery pin; and a flexible sheath. In some embodiments, a cannula extends through the delivery rod and the implant. In some embodiments, the implant includes a socket at a proximal end configured to engage a threaded distal end of the delivery rod.

In any of the preceding embodiments, the delivery pin is adapted to slide through a cannula extending through the delivery rod and the implant. The delivery pin can be configured to removably slide through the cannula. In some variations, the delivery pin is permanently attached to the implant. The delivery pin can be retractable in some cases. Additionally, the delivery pin can be configured to releasably attach to a distal end of the implant. In some variations, the delivery pin is adapted to disengage and slip into an interior of the implant. The delivery pin may have a length between about 5 mm to about 30 mm. In any of the preceding embodiments, a portion of the length of the delivery pin extends distal of a distal end of the implant. The portion of length can be between about 5 mm to about 30 mm.

In any of the preceding embodiments, the flexible sheath is adapted to protect soft tissue as the implant is advanced through bone, the flexible sheath having a plurality of outer wall portions forming a pyramidal tip at a distal end of the sheath. The pyramidal tip may be positioned at a distal end of the implant near the cutting broach. In some cases, the outer wall portions are angled at 60 degrees to form vertices of the pyramidal tip. In any of the preceding embodiments, the flexible sheath includes a tapered distal tip.

In any of the preceding embodiments, the broach is coupled to the core. In some embodiments, the broach includes a plurality of cutting edges located on a tapered distal end of the broach. In further embodiments, the broach includes teeth adapted to remove bone material as the implant is inserted through bone. In any of the preceding embodiments, the implant includes an outer surface having surface features configured to promote bony in-growth on the implant. In some embodiments, the surface features include fenestrations. In some variations the outer surface of the implant is porous. In any of the preceding embodiments, the surface features extend longitudinally along the outer surface between a proximal end and a distal end of the implant. In any of the preceding embodiments, the surface features include longitudinally extending ridges adapted to contact the two bones. In some cases, the surface features include a porous plasma spray coating. In other embodiments, the surface features include a surface coating having a biologic aid for promoting bony in-growth. A biologic aid includes growth factors or a controlled release formulation.

In any of the preceding embodiments, the implant includes a geometric configuration adapted to resist loosening during movement. The geometric configuration may be a triangular cross-section, rectilinear cross-section, or curvilinear cross-section.

In any of the preceding embodiments, the delivery rod includes a protrusion configured to control advancement through bone. In any of the preceding embodiments, the implant includes a safety protrusion configured to indicate implant insertion depth. In some embodiments, the implant includes a safety marking to indicate implant insertion depth.

Other embodiments provide for a bone fusion implant having a core adapted for placement between two bones, the core having a first end and a second end; and a cutting broach at the second end of the core. In some embodiments, the broach is coupled to the core. The broach may include a plurality of cutting edges located on a tapered distal end of the broach. In some cases, the broach includes teeth adapted to remove bone material as the implant is inserted through the two bones.

In any of the preceding embodiments, the implant includes an outer surface having surface features configured to promote bony in-growth on the implant. In some embodiments, the surface features include fenestrations. In some variations the outer surface of the implant is porous. In any of the preceding embodiments, the surface features extend longitudinally along the outer surface between a proximal end and a distal end of the implant. In any of the preceding embodiments, the surface features include longitudinally extending ridges adapted to contact the two bones. In some cases, the surface features include a porous plasma spray coating. In other embodiments, the surface features include a surface coating having a biologic aid for promoting bony in-growth. A biologic aid includes growth factors or a controlled release formulation.

In any of the preceding embodiments, the implant includes a socket on the first end of the core, the socket adapted to couple to a delivery tool configured to deliver the implant into bone.

In any of the preceding embodiments, the implant includes a delivery pin permanently attached to the implant. In some cases, the delivery pin is retractable. In other cases, the delivery pin has a length between about 5 mm to about 30 mm. In some cases, a portion of the length of the delivery pin extends distal of a distal end of the implant. The portion of length may be between about 5 mm to about 30 mm.

In any of the preceding embodiments, the implant may include a delivery pin configured to releasably attach to a distal end of the implant. In some cases, the delivery pin is adapted to disengage and slip into an interior of the implant.

In any of the preceding embodiments, the implant includes a geometric configuration adapted to resist loosening during movement. The geometric configuration may be a triangular cross-section, rectilinear cross-section, or curvilinear cross-section.

In any of the preceding embodiments, the implant has a length between about 30 mm to about 70 mm.

In any of the preceding embodiments, the implant includes a safety protrusion configured to indicate implant insertion depth. In some embodiments, the implant includes a safety marking to indicate implant insertion depth.

Further embodiments provide for an integrated implant delivery assembly having a bone fusion implant including a core; a cutting broach at a distal end of the core; and a cutting burr having a cutting assembly configured to remove and cut through bone; and a delivery pin assembly having a delivery pin and a driving device, the delivery pin assembly configured to be partially received within the cutting burr to rotationally drive the cutting burr.

In any of the preceding embodiments, the driving device and the delivery pin are separate interlocking components. In some cases, the driving device and the delivery pin are fused to form a single component. In other variations, the length of the driving device is between about 30 mm and 150 mm. In further embodiments, the delivery pin is configured to be slidably received within a cannula of the cutting burr, the delivery pin adapted to extend distally from a distal end of the cutting burr.

In any of the preceding embodiments, the driving device includes a drive socket; drive shaft, and a drive member configured to engage an implant socket at a proximal end of the implant to rotationally lock therewith. The driving member can be configured to rotationally drive the cutting burr when engaged with the implant socket.

In any of the preceding embodiments, the delivery pin includes a pin socket configured to engage with the drive member of the driving device and a pin shaft extending distally from the pin socket. In some cases, the pin socket is configured to be rotationally driven by the driving device when engaged with the drive member. In further embodiments, the pin socket includes a tapered distal point. In other variations, the length of the pin shaft is about 30 mm to about 90 mm. In any of the preceding embodiments, the pin shaft extends beyond a distal end of the cutting burr by a length between about 5 mm to about 30 mm.

In any of the preceding embodiments, the drive socket is configured to receive a drill member, the drill member coupled to a draft shaft and a drill. The drill may be an impact drill. The drill shaft may be configured to rotationally drive the drill member to thereby rotationally drive the driving device while the drill member is engaged in the drive socket.

In any of the preceding embodiments, the cutting burr is positioned along a central axis of the implant and extends through the core and the cutting broach. The cutting burr can be configured to rotate while positioned inside the core. In some variations, the cutting burr is configured to rotate while positioned inside the cutting broach. In further variations, the cutting burr is configured to be collapsible and removable by retraction.

In any of the preceding embodiments, the cutting burr includes an expanded configuration and a collapsed configuration, the cutting burr adapted to transition to the collapsed configuration by retraction. In any of the preceding embodiments, the cutting burr is adapted to extend beyond a distal end of the implant. In any of the preceding embodiments, the cutting burr is adapted to extend a length between about 5 mm to about 20 mm beyond the distal end of the implant.

In any of the preceding embodiments, the cutting assembly includes a set of centrifugal blades, the blades having an expanded state and a retracted state, the blades extending beyond a distal end of the implant in the expanded state and the blades retracted inward of the distal end of the implant in the retracted state.

In any of the preceding embodiments, the cutting assembly includes a plurality of cutting blades extending radially outward from the center of the cutting assembly. In any of the preceding embodiments, the plurality of cutting blades are hinged to thereby expand and collapse the cutting assembly. In any of the preceding embodiments, the cutting blades are configured to bore through bone.

Further embodiments provide for a bone fusion implant having a core having a first end and a second end; a cutting broach at the second end of the core; and a cutting burr having a cutting assembly configured to remove and cut through bone.

In any of the preceding embodiments, the cutting burr is positioned along a central axis of the implant and extends through the core and the cutting broach. In some cases, the cutting burr is configured to rotate while positioned inside the core. In any of the preceding embodiments, the cutting burr is configured to rotate while positioned inside the cutting broach. Additionally, the cutting burr may be fixed translationally on a center axis of the implant.

In any of the preceding embodiments, the cutting burr includes an expanded configuration and a collapsed configuration, the cutting burr adapted to transition to the collapsed configuration by retraction. In any of the preceding embodiments, the cutting burr is adapted to extend beyond a distal end of the implant. In any of the preceding embodiments, the cutting burr is adapted to extend a length between about 5 mm to about 20 mm beyond the distal end of the implant. In any of the preceding embodiments, the cutting burr is configured to be collapsible and removable by retraction.

In any of the preceding embodiments, the cutting burr further includes a socket positioned at a proximal end of the cutting burr; a cannula extending between the cutting assembly and the socket, and a shaft coupled to the socket and residing in the cannula. In some embodiments, the socket includes an interior surface having a square or hexagon shape. The socket may be configured with an interior surface adapted to fit and receive a driving device. In further embodiments, the socket is configured to impart a rotational driving force from the driving device to the shaft.

In any of the preceding embodiments, the shaft includes a channel adapted to move bone debris into an interior of the implant.

In any of the preceding embodiments, the cutting assembly includes a plurality of cutting blades extending radially outward from the center of the cutting assembly. In any of the preceding embodiments, the plurality of cutting blades are hinged to thereby expand and collapse the cutting assembly. In any of the preceding embodiments, the cutting blades are configured to bore through bone.

In any of the preceding embodiments, the broach is coupled to the core. The broach may include a plurality of cutting edges located on a tapered distal end of the broach. Additionally, the broach may include teeth adapted to remove bone material as the implant is inserted through the two bones.

In any of the preceding embodiments, the implant includes an outer surface having surface features configured to promote bony in-growth on the implant. In some embodiments, the surface features include fenestrations. In some variations the outer surface of the implant is porous. In any of the preceding embodiments, the surface features extend longitudinally along the outer surface between a proximal end and a distal end of the implant. In any of the preceding embodiments, the surface features include longitudinally extending ridges adapted to contact the two bones. In some cases, the surface features include a porous plasma spray coating. In other embodiments, the surface features include a surface coating having a biologic aid for promoting bony in-growth. A biologic aid includes growth factors or a controlled release formulation.

In any of the preceding embodiments, the implant includes a socket on the first end of the core, the socket adapted to couple to a delivery tool configured to deliver the implant into bone.

In any of the preceding embodiments, the implant may include a delivery pin permanently attached to the implant. In some cases, the delivery pin is retractable. The delivery pin may have a length between about 5 mm to about 30 mm. In some cases, the delivery pin is configured to releasably attach to a distal end of the implant. In any of the preceding embodiments, the delivery pin is adapted to disengage and slip into an interior of the implant. In any of the preceding embodiments, the pin may extend beyond a distal end of the cutting burr by a length between about 5 mm to about 30 mm.

In any of the preceding embodiments, the implant may include geometric configuration adapted to resist loosening during movement. These include a triangular, rectilinear, and curvilinear cross-section.

In any of the preceding embodiments, the implant may include a safety protrusion configured to indicate implant insertion depth. In any of the preceding embodiments, the implant may include a safety marking to indicate implant insertion depth.

Further embodiments provide for a bone fusion implant having a core having a hollow structure formed by a multi-sided wall; a delivery pin hole within the core extending from a proximal end to a distal end of the core; and a plurality of cutting edges at a distal end of the multi-sided wall.

In any of the preceding embodiments, the multi-sided wall includes a plurality of interlocking wall sections. In some cases, the plurality of interlocking wall sections include interlocking edges, the wall sections configured to be implanted independently and interlocked after insertion into a patient. In any of the preceding embodiments, the multi-sided wall has a thickness between about 0.5 mm to about 5 mm. In any of the preceding embodiments, the multi-sided wall is formed from a plurality of wall portions, each wall portion having a tapering distal end. In any of the preceding embodiments, the tapering distal end forms a point at the center of the tapering distal end of each wall portion. In any of the preceding embodiments, the tapering distal end forms a vertex between intersecting wall portions. In some embodiments, the tapering distal end forms a jagged cutting edge at the distal end of the multi-sided wall.

In any of the preceding embodiments, the surface area of the implant gradually increases with distance moving from the tapering distal end toward a proximal end of the implant.

In any of the preceding embodiments, the cutting edges are corrugated or tapered. In any of the preceding embodiments, the cutting edges are positioned on an interior surface of the multi-sided wall. In other embodiments, the cutting edges are configured to cut bone and pass cut bone through the core.

In any of the preceding embodiments, the core is formed from three wall portions having a first hollow triangular member, a second hollow triangular member, and a connecting member attached to the first and second triangular members. In some cases, wherein the first and second members are coupled together at an apex point for each triangular member.

In any of the preceding embodiments, the implant includes a bow-tie shaped cross-section.

In any of the preceding embodiments, the thickness of the three wall portions is between about 0.5 mm to about 5 mm.

In any of the preceding embodiments, the length of the implant is between about 30 mm to about 70 mm.

In any of the preceding embodiments, the implant includes an I-shaped cross-section.

In any of the preceding embodiments, the core is formed from three wall portions having a first elongate member, a second elongate member, and a third elongate member, the first and second members positioned relatively parallel to one another and the third elongate member intersecting the first and second members to couple the three members together.

In any of the preceding embodiments, the third elongate member perpendicularly intersects the first and second members.

In any of the preceding embodiments, the implant has a tri-legged cross-section. In any of the preceding embodiments, the implant has a T-shaped cross-section. In any of the preceding embodiments, the implant has a X-shaped cross-section. In any of the preceding embodiments, the implant has a rectilinear cross-section. In any of the preceding embodiments, the implant has a curved cross-section.

Further embodiments describe methods for fusing bone. These methods include identifying a bone site having a first bone segment, a second bone segment, and a non-bony region between the first and second bone segments; providing a bone fusion implant having a core with a distal end and cutting broach on the distal end of the core; inserting a delivery pin through a first bone segment and into a second bone segment, wherein the delivery pin is inserted partially through the second bone segment; forming a pilot insertion bore in the first and second bone segments; and inserting the implant into the first and second bone segments to thereby fuse the bone segments, wherein inserting the implant advances the cutting broach through the bore and cuts at least one edge of the bore to accommodate the implant shape.

In any of the preceding embodiments, the method may include inserting the implant entirely through the first bone segment and non-bony region and partially through the second bone segment.

Additionally, any of the preceding embodiments may include passing a cannulated drill bit over the delivery pin and forming the pilot insertion bore with the cannulated drill.

In any of the preceding embodiments, the implant further includes a cutting burr on the distal end of the core.

In any of the preceding embodiments, forming a pilot insertion bore includes advancing the cutting burr into the first and second bone segments.

Additionally, any of the preceding embodiments may include generating the pilot insertion bore by tapping the implant into the first and second bone segments.

In any of the preceding embodiments, inserting the implant further includes tapping a delivery rod engaged with the implant to form a pilot insertion bore with the cutting burr.

Additionally, any of the preceding embodiments may include rotationally driving the cutting burr to form the pilot insertion bore.

Additionally, any of the preceding embodiments may include retracting the cutting bore into an interior of the implant.

Additionally, any of the preceding embodiments may include an implant with a triangular cross-section.

Additionally, any of the preceding embodiments may include an implant with an I-shaped cross-section.

In any of the preceding embodiments for fusing bone, the first bone segment is the ilium and the second bone segment is the sacrum.

In any of the preceding embodiments for fusing bone, the steps may include inserting the implant laterally through the ilium and into the sacrum.

In any of the preceding embodiments for fusing bone, the steps may include inserting a plurality of implants laterally through the ilium and into the sacrum.

Additional embodiments provide for methods for fusion of the sacral-iliac joint between an iliac and a sacrum. These methods include providing an integrated implant delivery assembly and a delivery pin; inserting the delivery pin laterally through the ilium and into the sacrum; sliding the flexible sheath over the delivery pin to protect soft tissue around the delivery pin; tapping the implant into the ilium, through the sacral-iliac joint, and into the sacrum.

In any of the preceding embodiments, the assembly may include a flexible sheath and a bone fusion implant having a core and a cutting broach on a distal end of the core.

In any of the preceding embodiments, the method may include forming a pilot insertion bore by the tapping the implant into the ilium, through the sacral-iliac joint, and into the sacrum.

In any of the preceding embodiments, the method may include broaching the bore by advancing the implant through the bore. In any of the preceding embodiments, the implant further includes a cutting burr at the distal end of the core.

In any of the preceding embodiments, the method may include rotationally driving the cutting burr to generate a pilot insertion bore. In any of the preceding embodiments, the method may include retracting the cutting burr inside the implant after generating the bore.

In any of the preceding embodiments, the method may include positioning the implant to be flush with a lateral wall of the ilium. In any of the preceding embodiments, the method may include positioning a proximal end of the implant to extend about 1 mm to about 5 mm outside of the ilium.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 14A-D are anatomic views of implanted exemplary integrated implants.

DETAILED DESCRIPTION

Reference will now be made in detail to exemplary embodiments of the invention, examples of which are illustrated in the accompanying drawings. While the invention will be described in conjunction with the exemplary embodiments, it will be understood that they are not intended to limit the invention to those embodiments. On the contrary, the invention is intended to cover alternatives, modifications and equivalents, which may be included within the spirit and scope of the invention as described herein.

Various aspects of the present invention relate to an integrated implant having a cutting broach and/or cutting burr. In various embodiments, the integrated implants may be used to fuse the sacroiliac joint. Integrated implants discussed herein may also be used to fuse other bones within a human patient. For example, the integrated implant may be used to fuse the lumbar region of the spine and other bones. As such, those of ordinary skill in the art will realize that exemplary embodiments related to sacroiliac joint fusion are not limited to this type of fusion, but rather set forth as examples.

Figure 1A:
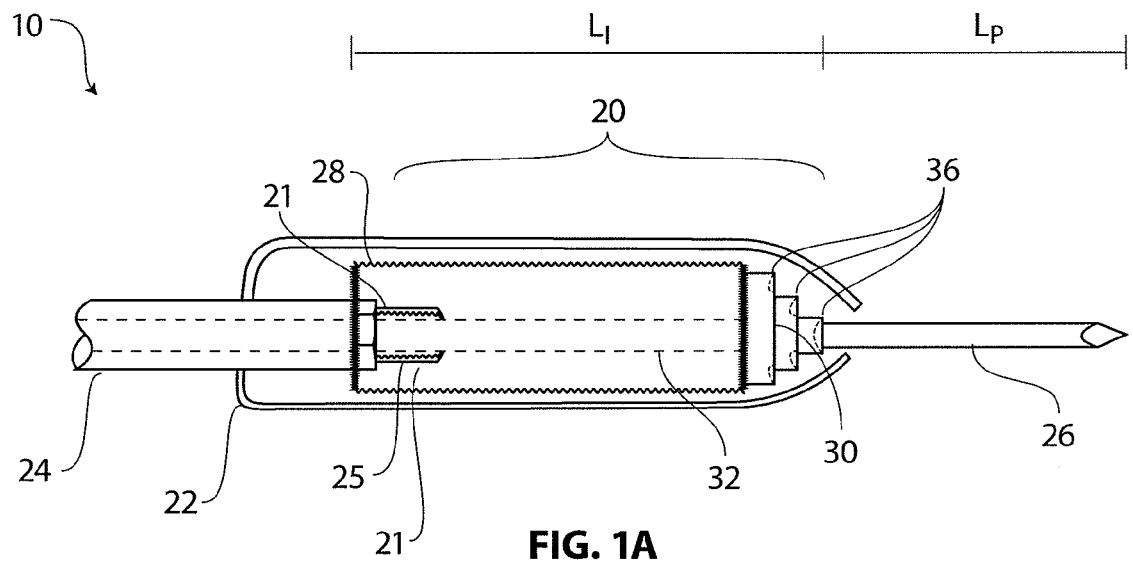
FIG. 1A is a longitudinal section view of an exemplary integrated implant assembly.

FIG. 1A is a longitudinal sectional view of an exemplary integrated implant assembly. The integrated implant assembly 10 includes an integrated implant 20, a flexible sheath 22, a delivery rod 24, and a delivery pin 26. Delivery rod 24 and integrated implant 20 may be cannulated. Canula 32 may provide access for the delivery pin 26. The delivery rod 24 may include a threaded distal end 25 that may have a radius that is smaller than the radius of the delivery rod 24. The threaded distal end 25 may engage the integrated implant socket 21. Integrated implant 20 may include a socket 21, core 28 and a cutting broach 30. The core 28 may have a proximal end and a distal end, where the terms distal and proximal are used with respect to outer end of the delivery rod (the portion of the delivery rod that does not engage the integrated implant socket 21). The distal end of the core 28 is coupled to the cutting broach 30. The cutting broach 30 may eliminate the need to take additional steps of drilling and broaching the bone or broaching the bone in an independent step. In various embodiments, the cutting broach 30 may be coupled to the core 28 by welding, independent fasteners, press-fit, threads, or other methods. In various embodiments, the cutting broach 30 and the core 28 may be generated as a single piece by machining, molding, extrusion or other methods.

Integrated implant 20 may be formed from a durable material usable in the prosthetic arts that is not subject to significant bio-absorption or resorption by surrounding bone or tissue over time. Integrated implant 20 is intended to remain in place for a time sufficient to stabilize the fracture or fusion site. Integrated implant 20 may also remain in place in the patient permanently. Such materials include, but are not limited to, titanium, titanium alloys, tantalum, tivanium (aluminum, vanadium, and titanium), chrome cobalt, surgical steel, or any other total joint replacement metal and/or ceramic, sintered glass, artificial bone, any uncemented metal or ceramic surface, or a combination thereof. Alternatively, the integrated implant 20 may be formed from a suitable durable biologic material or a combination of metal and biologic material, such as a biocompatible bone-filling material. The integrated implant 20 may be molded from a flowable biologic material, e.g., acrylic bone cement, that is cured, e.g., by UV light, to a non-flowable or solid material. e.g. polymers such as PLA, PLGA, PGA, or other similar materials.

The integrated implant 20 may be sized according to the local anatomy. The morphology of the local structures can be generally understood by medical professionals using textbooks of human skeletal anatomy along with their knowledge of the site and its disease or injury. The physician is also able to ascertain the dimensions of the appropriately sized integrated implant 20 based upon prior analysis of the morphology of the targeted bone region using, for example, plain film x-ray, fluoroscopic x-ray, or MRI or CT scanning, as well as intraoperative sizing methods using provided instrumentation. In various embodiments, the length of the integrated implant $L_I$ is in the range of about 30 mm to 70 mm. In various embodiments, the length of the integrated implant $L_I$ is about 30 mm, 35 mm, 40 mm, 45 mm, 50 mm, 55 mm, 60 mm, 65 mm, and 70 mm.

The integrated implant 20 may take various shapes and have various cross-sectional geometries. The integrated implant 20 may have a generally curvilinear (e.g., round or oval) cross-section or a generally rectilinear cross section (e.g., square or rectangular or triangular) or combinations thereof. The shape of integrated implant 20 is further discussed with respect to FIGS. 4-7M.

Figure 2A:
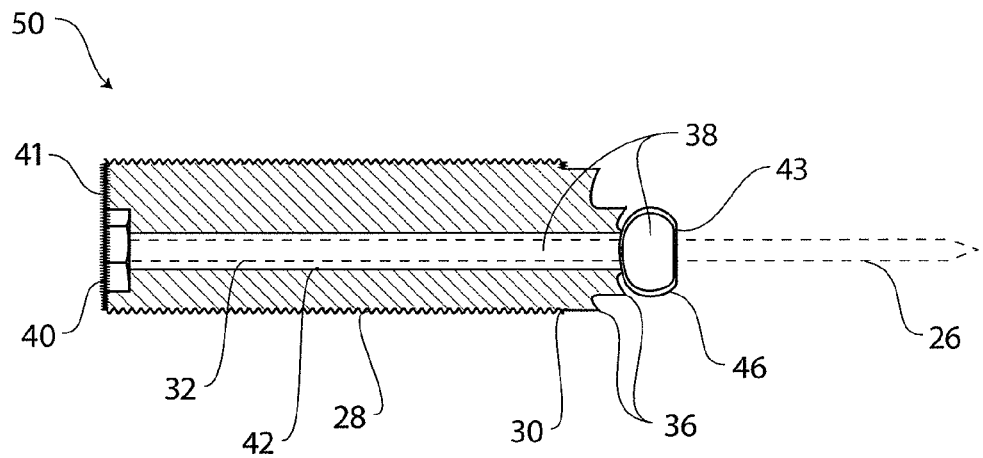
FIG. 2A is a longitudinal sectional view of another exemplary integrated implant.

In FIGS. 1A and 2A, the integrated implants 20, 50 are illustrated with a triangular shape, which may effectively improve implant stability. Implant stability may be defined as the ability of the implant to resist loads in the axial, lateral and rotational directions without loosening. The ability of the implant to withstand these loads while maintaining the stability is important. Primary implant stability is achieved at the time of surgery and may depend on the implant design. Primary implant stability may be influenced by implant geometry. An implant having a triangular geometry may resist rotation, migration and micromotion once implanted and may provide advantages over other geometries. While the initial stability may be related to mechanical features, the bone healing process eventually dictates long-term stability.

Secondary implant stability, which is achieved over time, may depend on the level of primary stability and the biological response to the surgery and implant. Newly formed bone tissue may fill voids at the implant/bone interface, create direct contact with the implant surface, and engage with surface irregularities. This interlocking effect is amplified when the newly formed bone matures over time.

The outer surface of the integrated implant 20 may have longitudinal channels that extend from the distal end to the proximal end. In various embodiments, the outer surface of the integrated implant 20 is corrugated having a series of parallel ridges and furrows (not shown) that extend longitudinally between the proximal and distal ends. The channels, corrugations and furrows may increase the bony contact area between the bones and implant 20

Additionally, integrated implant 20 may have a portion on the outer surface that is conducive to bony in-growth, on-growth, or through-growth. In various embodiments, the portion may include the entire outer surface of the integrated implant 20. The bony in-growth, on-growth, or through-growth portion may include through holes, various surface patterns, various surface textures, and/or pores, or combinations thereof. In various embodiments, the outer surface may have a mesh configuration, beaded configuration, trabecular configuration, holes or fenestrations or any surface conducive to bony through-growth.

The outer surface of the integrated implant 20 may be coated, wrapped or surface treated to promote the bony in-growth or through-growth. In various embodiments, the coating material can include a biologic aid that can promote and/or enhance bony ingrowth, tissue repair, and/or reduce inflammation, infection and pain. The biologic aid may include growth factors, such as bone morphogenetic proteins (BMPs), hydroxyapatite in a liquid or slurry carrier, demineralized bone, morselized autograft or allograft bone, medications to reduce inflammation, infection and pain such as analgesics, antibiotics and steroids. In various embodiments, the growth factors may be human recombinant growth factors, such as rh-BMP-2 and/or rh-BMP-7, or any other human recombinant form of BMP. The carrier for the biologic aid may be a liquid or gel such as saline or a collagen gel. The biologic aid may also be encapsulated or incorporated in a controlled released formulation so that the biologic aid is released to the patient at the implant site over a longer duration. For example, the controlled release formulation may be configured to release the biologic aid over the course of days, weeks or months, and can be configured to release the biologic aid over an estimated time it would take for the implant site to heal. The amount of biologic aid delivered to the integrated implant 20 may be controlled using a variety of techniques, such as controlling or varying the amount of coating material applied to the integrated implant 20 and/or controlling or varying the amount of biologic aid incorporated into the coating material. Controlling the amount of biologic aid delivered may be important because excessive use of certain biologic aids may result in negative effects such as localized inflammation, local pain, or radicular pain.

In a various embodiments, the bony in-growth portion, on-growth, or through-growth portion comprises a porous plasma spray coating on the integrated implant 20. The coating may create a biomechanically rigorous fixation/fusion system, designed to support reliable fixation/fusion and acute weight bearing capacity.

Alternatively, the outer surface may be formed from a material that itself inherently possesses a structure conducive to bony in-growth or through-growth, such as a porous mesh, hydroxyapetite, or other porous surface.

The bony in-growth or through-growth portion may further be covered with various other coatings such as antimicrobial, antithrombotic, and osteoinductive agents, or a combination thereof. In various embodiments, the entire integrated implant 20 may be impregnated with such agents.

The delivery pin 26 of the integrated implant assembly 10 shown in FIG. 1A may have a pointed or blunt tip at the distal end. The delivery pin 26 may be permanently attached to the integrated implant 20. The permanently attached delivery pin 26 may be retractable or may disengage and slip inside the integrated implant 20. Alternatively, the delivery pin 26 may be removable. In various embodiments, the delivery pin 26 may be part of the integrated implant 20 or part of a delivery rod 24. In various embodiments, the length $L_P$ of the delivery pin 26 is in the range of about 0 mm to 30 mm. In various embodiments, the length $L_P$ of the delivery pin 26 is about 0 mm, 5 mm, 10 mm, 15 mm, 20 mm, 25 mm and 30 mm. In various embodiments, the length $L_P$ of the delivery pin 26 extends beyond the distal end of the integrated implant 20 by a distance of about 0 mm to 30 mm. In various embodiments, the length $L_P$ of the delivery pin 26 extends beyond the distal end of the integrated implant 20 by a distance of about 0 mm, 5 mm, 10 mm, 15 mm, 20 mm, 25 mm, and 30 mm.

Figure 1B:
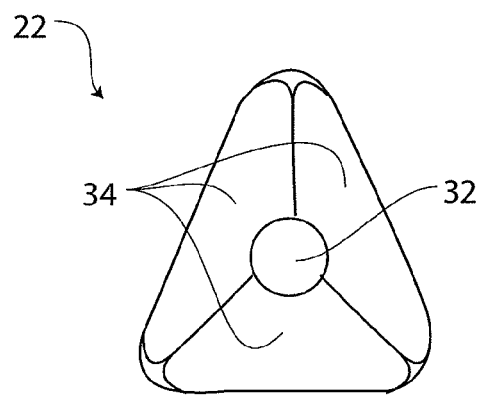
FIG. 1B is an enlarged front view of the distal end of a flexible sheath of FIG. 1A.

FIG. 1B is an enlarged front view of the distal end of a flexible sheath of FIG. 1A. The flexible sheath 22 may be used as a delivery sheath that may protect soft tissue as the integrated implant 20 is advanced. The flexible sheath 22 may have a tip formed at the distal end that forces expansion when it is tapped against bone. The design of the tip of the flexible sheath 22 may provide easy insertion through soft tissue. The flexible sheath 22 includes outer wall portions 34. Outer wall portions 34 can be angled at, for example, approximately 60 degrees to form vertices of a triangle. The outer wall portions 34 may be substantially planar forming a pyramidal tip at the distal end. The flexible sheath may be formed from one or more of a thermoplastic polyethylene (e.g. ultra-high molecular weight polyethylene, high-modulus polyethylene or high-performance polyethylene), organic polymer thermoplastic (e.g. polyether ether ketone), thermoset polymer, elastomer and other material.

Figure 1C:
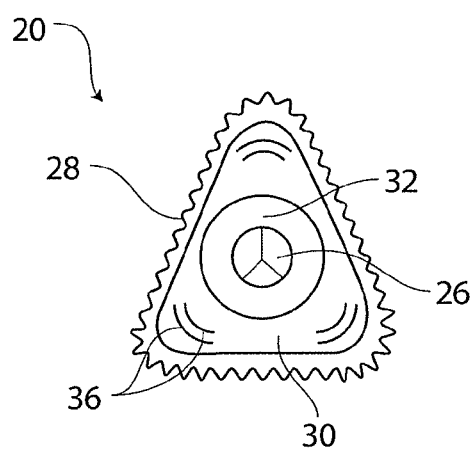
FIG. 1C is an enlarged front view of the distal end of the integrated implant of FIG. 1A.

FIG. 1C is an enlarged front view of the distal end of the integrated implant of FIG. 1A. The integrated implant 20 includes delivery pin 26, core 28, cutting broach 30 and canula 32. Cutting broach 30 may include broaching edges 36. The broaching edges 36 may be located on a tapered distal end of the cutting broach 30. The broaching edges 36 may include teeth used to remove bone material when the integrated implant 20 is inserted linearly.

In various embodiments, integrated implant assembly 10 includes a cannulated delivery rod 24 and cannulated integrated implant 20 that is used with a standard delivery pin 26, for example a Steinman pin. In various embodiments, the integrated implant assembly 10 includes a delivery pin 26 that is coupled to the integrated implant 20. There may be no canula 32 within integrated implant 20 or delivery rod 24. In various embodiments, integrated implant assembly 10 includes a delivery rod 24 and a cannulated integrated implant 20. Delivery rod 24 may be coupled to delivery pin 26.

FIG. 2A is a longitudinal sectional view of another exemplary integrated implant. The integrated implant 50 of FIG. 2A includes core 28 and cutting broach 30 of FIGS. 1A and 1C. The integrated implant 50 may also be coupled to a cutting burr 38. Cutting burr 38 may have a canula 32, and may include socket 40, shaft 42, and cutting assembly 46. The cutting burr 38 may be formed from the same materials as integrated implant 20 of FIG. 1A. Cutting burr 38 may extend between the proximal end 41 and the distal end 43 of the integrated implant 50 and may be positioned within the integrated implant 50, for example along the center axis of the integrated implant 50. In various embodiments, the cutting burr 38 is part of the integrated implant structure and configured to move rotationally while within the center of the integrated implant 50. In various embodiments, the cutting burr 38 is fixed translationally within the center of the integrated implant 50. When the cutting burr 38 is part of the integrated implant 50, the cutting burr 38 may remain implanted.

In various embodiments, the cutting burr 38 is collapsible and removable by retraction. Cutting burr 38 may extend beyond the distal end of integrated implant 50. In various embodiments, the cutting burr 38 may extend beyond the distal end of the integrated implant 50 a distance in the range of about 0 mm and 20 mm. In various embodiments, may extend beyond the distal end of the integrated implant 50 a distance of 0 mm, 5 mm, 10 mm, 15 mm, and 20 mm.

Socket 40 is positioned at the proximal end of the cutting burr 38 and may include an opening or a hollow cavity into which an inserted part is designed to fit. The interior surface of the socket 40 may form a geometrical shape such as a square, hexagon or other geometrical shape. In various embodiments, the interior surface of socket 40 is designed to fit and receive a driver or driving device. Socket 40 may be coupled to the shaft 42 for imparting a rotational driving force from a driver to shaft 42. The shaft 42 may extend longitudinally from the distal end of the socket 40 to the proximal end of the cutting assembly 46.

Cutting assembly 46 may include an arrangement of a plurality of cutting blades 48 (shown in FIG. 2B) that extend radially outward and that may be mounted for rotation about a central axis. During operation, the cutting blades 48 may extend outward in front of the cutting broach 30 to remove and cut through bone. The cutting blades 48 may be hinged so that they are expandable and collapsible. The cutting blades 48 may be attached to a flange. The cutting blades 48 may be retracted inside of the integrated implant 50 after bone removal is complete. One or more channels may be provided in shaft 42 and/or in core 28 to permit bone chips created by cutting blades 48 to move away from the cutting area and into the integrated implant. The removed bone chips may be evacuated from the implant by the used of helical flutes, suction, gas pressure, introduction of irrigation fluid, and/or other means. Integrated implant 50 may be configured such that some or all of the cut bone chips remain within the implant and/or are directed to surface portions of the implant to aid in healing and bony-ingrowth into the implant.

Generally, the cutting broach 30 may be used to cut pointed or angulated corners of bone and the cutting burr 38 may used to cut the main diameter of bone. The core 28, cutting broach 30 and cutting burr 38 of integrated implant 50 may be formed in a similar manner to that of integrated implant 20 of FIG. 1A-C. The formation may include constructing an integrated implant from a similar material and using a similar molding and sizing process as described with respect to FIG. 1A-C.

Figure 2B:
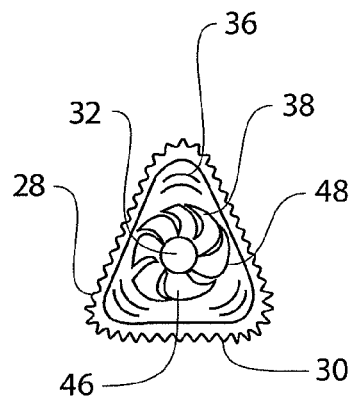
FIG. 2B is an enlarged front view of the distal end of the integrated implant of FIG. 2A.

FIG. 2B is an enlarged front view of the distal end of the integrated implant of FIG. 2A. The integrated implant 50 includes core 28, cutting broach 30, cutting burr 38 and canula 32. Cutting broach 30 may include broaching edges 36. The broaching edges 36 may be located on a tapered distal end of the cutting broach 30. The broaching edges 36 may include teeth used to remove bone material when the integrated implant 50 is inserted linearly. Cutting burr 38 may include cutting assembly 46 with cutting blades 48 to bore through the bone.

Figure 3:
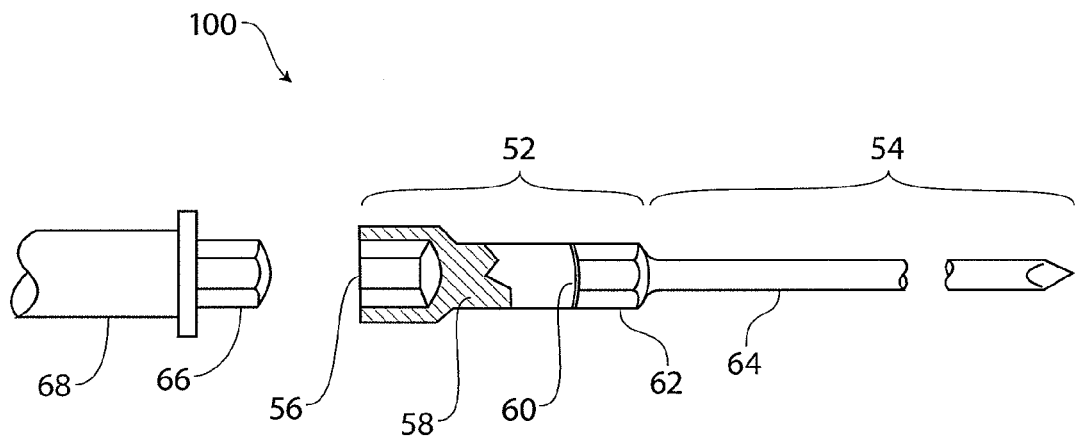
FIG. 3 is a side view of an integrated delivery pin assembly.
Figure 4:
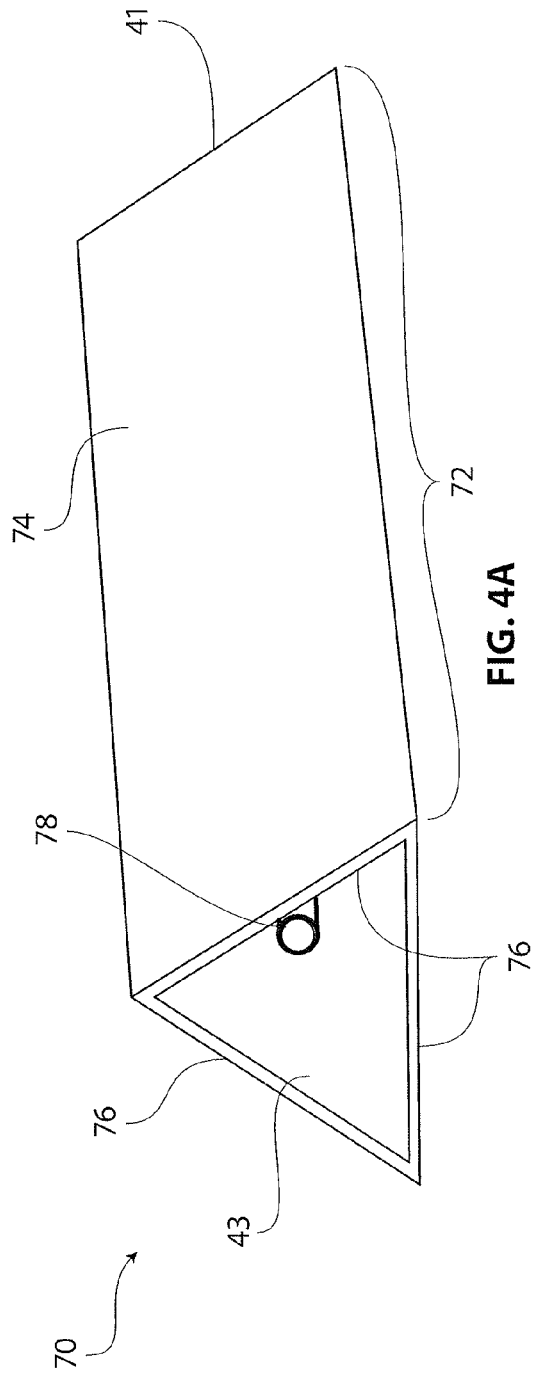
FIGS. 4A-F are isometric views of exemplary hollow integrated implants.

FIG. 3 is a side view of an integrated delivery pin assembly. The integrated delivery pin assembly 100 may include driving device 52 and a delivery pin 54. The driving device 52 may include a drive socket 56, drive shaft 58, and drive member 60. The delivery pin 54 may include a pin socket 62 and pin shaft 64. The integrated delivery pin assembly 100 of this embodiment is configured to be partially received within cutting burr 38 to rotationally drive the cutting burr. Specifically, the delivery pin 54 is configured to be slidably received within cannula 32 of cutting burr 38 and to extend from the distal end of cutting burr 38, as depicted by the dashed lines in FIG. 2A. Drive member 60 is configured to be slidably received within implant socket 40, shown in FIG. 2A, and rotationally lock therewith. The drive socket 56 may receive or fit a drill member 66. The drill member 66 is coupled to a drill shaft 68 and drill (not shown). In various embodiments, the drill is an impact drill.

In various embodiments, the driving device 52 and delivery pin 54 may be separate pieces that may be assembled. In operation, the drill shaft 68 turns in a rotational direction which drives the drill member 66 in a rotational direction. Drill member 66 engages drive socket 56 and drives the driving device 52 in a rotational direction. The interior surface of the drive socket 56 may form a geometrical shape such as a hexagon or other geometrical shape. A drive shaft 58 extends longitudinally between the distal end of the drive socket 56 and proximal end of the drive member 60. The drive member 60 may engage the pin socket 62.

Pin socket 62 is driven by the drive member 60 in a rotational direction. The interior surface of the pin socket 62 may form a geometrical shape such as a hexagon or other geometrical shape. The distal end of the pin socket 62 may be coupled to a pin shaft 64 that has a length of $L_S$. The distal end the pin shaft 64 may form a point. In various embodiments, the length $L_S$ of pin shaft 64 is in a range of about 30 mm to 90 mm. In various embodiments, the length $L_S$ of pin shaft 64 is about 30 mm, 35 mm, 40 mm, 45 mm, 50 mm, 55 mm, 60 mm, 65 mm, 70 mm, 75 mm, 80 mm, 85 mm, and 90 mm.

Delivery pin assembly 100 may be used to implant integrated implant 50. Delivery pin assembly 100 may be formed from one or more of various metals, metal alloys (e.g. stainless steel, titanium alloy), polymers, carbon fibers and other materials.

Alternatively, the driving device 52 and delivery pin 54 may be formed as a single piece or fused together to form a single piece. In operation, such as with integrated implant 50, an embodiment that includes a single driving member/delivery pin piece, the drill member 66 may engage the drive socket 56 and may move the single piece in a rotational direction. Drive socket 56 may be coupled to drive member 60. Drive member 60 may engage socket 40 on the proximal end of the cutting burr 38 (shown in FIG. 2A) and may drive the cutting burr 38 in a rotational direction.

In various embodiments, the length $L_S$ of the pin shaft 64 extends beyond the distal end of the cutting burr 38 by a distance of about 0 mm to 30 mm. In various embodiments, the length $L_S$ of the pin shaft 64 extends beyond the distal end of the cutting burr 38 by a distance of about 0 mm, 5 mm, 10 mm, 15 mm, 20 mm, 25 mm, and 30 mm. The length $L_S$ of the pin shaft 64 may be specific to the length of the integrated implant 50. The length $L_D$ of the driving device 52 may be the length which the integrated implant 50 will be driven into the bone. In various embodiments, the length $L_D$ of driving device 52 is a range of about 30 mm and 150 mm. In various embodiments, the length $L_D$ of driving device 52 is 30 mm, 60 mm, 90 mm, 120 mm, and 150 mm.

Integrated implants 20 and 50 may include a safety feature for preventing the implant from being driven too far into a patient. In various embodiments, the safety feature may include a marking, a protrusion, or some other feature on implants 20 and 50. The protrusion may be located on delivery rod 24 or drill shaft 68 and may come in contact with a patient's skin or outer ilium surface to prevent further advancement into the bone. The marking may be located on delivery rod 24 or drill shaft 68 and may indicate a measure of the insertion depth, for example depth gauge.

The integrated implant structures discussed with respect to FIGS. 4A-7M may be formed in a similar manner as integrated implant 20 of FIG. 1A-C. The formation may include constructing an integrated implant from a similar material and using a similar molding and sizing process as described with respect to FIG. 1A-C.

FIGS. 4A-E are side views of exemplary hollow integrated implants. The hollow integrated implant 70 of FIG. 4E includes a core 72 made up of three wall portions 74. The core 72 may be formed as one multiple-sided wall portion 74 or separate multiple interlockable wall portions 74. In various embodiments, multiple wall portions 74 are implanted independently and assembled by interlocking the wall portion edges. The distal end 43 of wall portion 74 may have a cutting edge 76. A delivery pin hole 78 may be within core 72 and may extend between distal end 43 and proximal end 41. In various embodiments, each delivery pin hole 78 may be formed from a structure that may be soldered or otherwise attached to an interior surface of a wall portion. In other embodiments, the delivery pin hole(s) may be integrally formed with the wall portion(s). The delivery pin hole(s) may be located at the edge(s) of the wall portion(s) and/or along the outside of the implant.

Cutting edges 76 may be implemented as a corrugated edge, razor edge, serrated edge or some other cutting edge. In various embodiments, the cutting edges 76 are tapered (See FIG. 4B). The cutting edges 76 may extend along a portion of distal end 43. For example, the cutting edges 76 may be positioned on the interior surface of wall portions 74 at the distal end 43 (not shown). Wall portions 74 having cutting edges 76 may be configured to cut through bone and allow the bone to pass through the hollow structure formed by wall portions 74.

Wall portions 74 may have fenestrations 80 conducive to bony in-growth. (See FIG. 4C) In various embodiments, wall portions 74 may be corrugated along the entire surface between the proximal end 41 and distal end 43. (See FIG. 4D) The exterior surface of wall portions 74 may be porous to promote bony in-growth or on-growth. In various embodiments, the thickness of the wall of wall portions 74 is about 1 mm. In various embodiments, the thickness of wall portions 74 is in the range of about 0.5 mm to 5 mm. In various embodiments, the length of integrated implant 70 is in the range of about 30 mm to 70 mm. In various embodiments, the length of the integrated implant 70 is about 30 mm, 35 mm, 40 mm, 45 mm, 50 mm, 55 mm, 60 mm, 65 mm, and 70 mm.

In various embodiments, the distal end 43 of each wall portion 74 may taper to one or more points. The integrated implants of FIG. 4E and FIG. 4F illustrate exemplary embodiments which include cutting edges 76, a core 72 and three wall portions 74 with tapered distal ends 82. In various embodiments, each of the tapered distal ends 82 form a point in the center of the distal end 43 of each wall portion 74 (FIG. 4E), or at the apexes of the triangular cross-section (FIG. 4F). The tapered distal ends 82 provide a gradually increasing surface area to facilitate driving the core 72 into bone.

Figure 5:
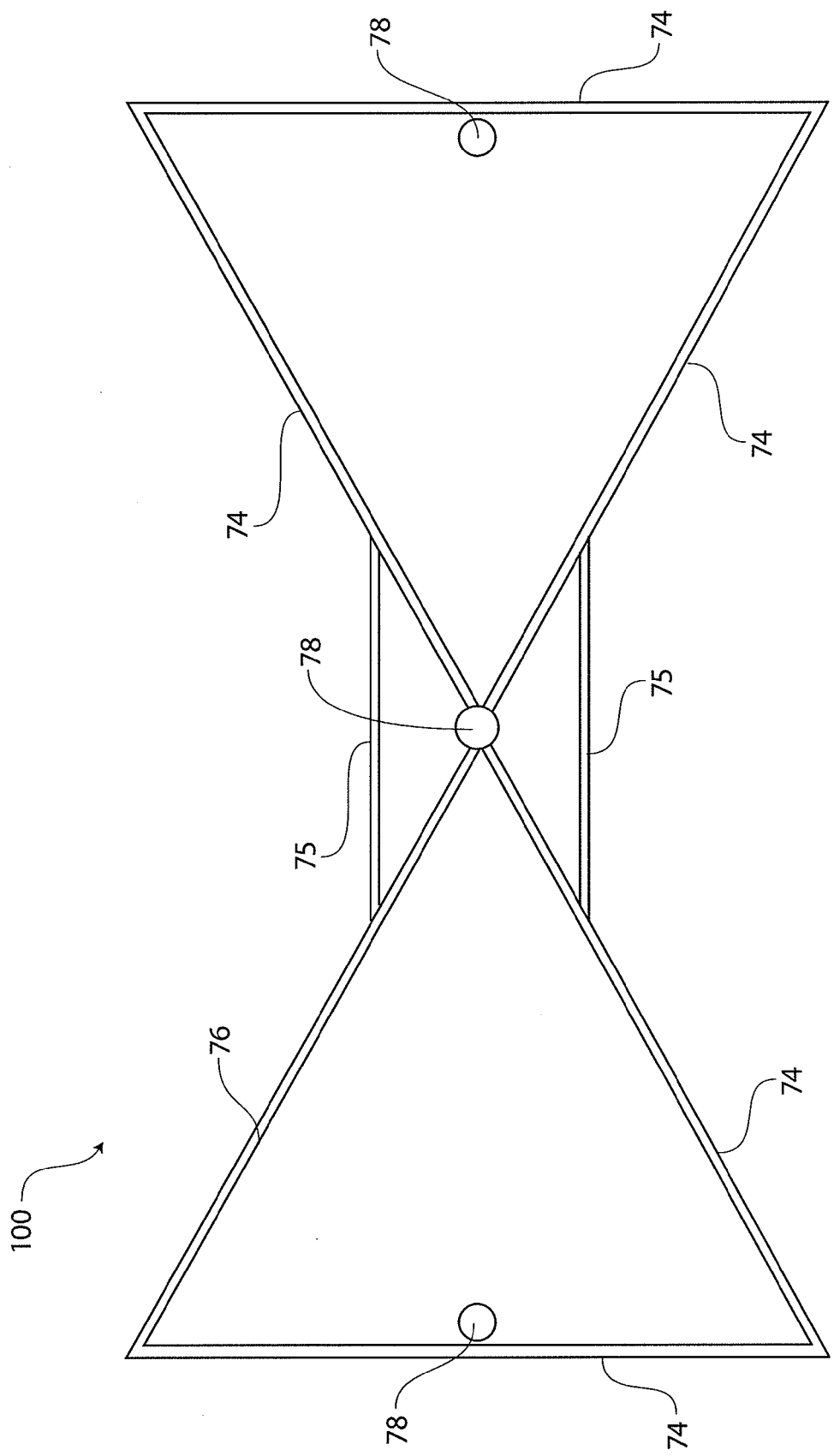
FIG. 5 is a front view of another hollow integrated implant.

FIG. 5 is a front view of another hollow integrated implant. The hollow integrated implant 100 includes wall portions 74, cutting edges 76 and delivery pin holes 78. Wall portions 74 may form a hollow shape similar to an I-beam. Each half of the I-beam may be formed by three wall portions 74 forming a triangle. The two triangles may be coupled together at an apex point for each triangle. An additional wall portion 75 may connect the two triangles on each side of the connected apex points. The two triangles couple together at an apex point to form a bow-tie shaped configuration. The thickness of the wall of wall portions 74 and 75 may be about 1 mm. In various embodiments, the thickness of wall portions 74 and 75 is in the range of about 0.5 mm to 5 mm. In various embodiments, the length of integrated implant 100 is in the range of about 30 mm to 70 mm. In various embodiments, the length of the integrated implant 100 is about 30 mm, 35 mm, 40 mm, 45 mm, 50 mm, 55 mm, 60 mm, 65 mm, and 70 mm.

The cutting edges 76 may be implemented on one or more of the wall portions 74. In various embodiments, each wall portion 74 may include a cutting edge 76. Each cutting edge 76 may be implemented as any of the cutting edges discussed with respect to FIGS. 4A-E.

The hollow integrated implant 100 may include one or more delivery pins 78. Each delivery pin hole may be configured to receive a delivery pin. In various embodiments, each delivery pin hole 78 may be formed from a structure that may be soldered or otherwise attached to or formed in an interior, middle or exterior region of a wall portion. Wall portions 74 having cutting edges 76 may be configured to cut through bone and allow the bone to pass through the hollow structure formed by wall portions 74.

Figure 6B:
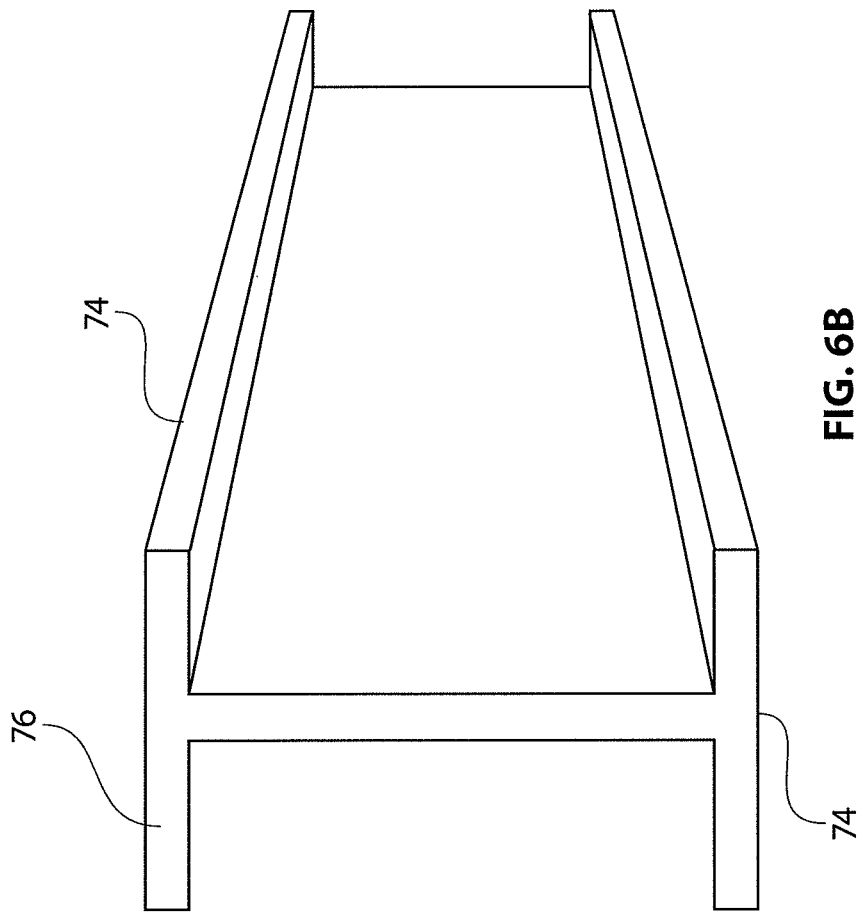
FIG. 6B is a perspective view of the integrated implant of FIG. 6A.
Figure 6A:
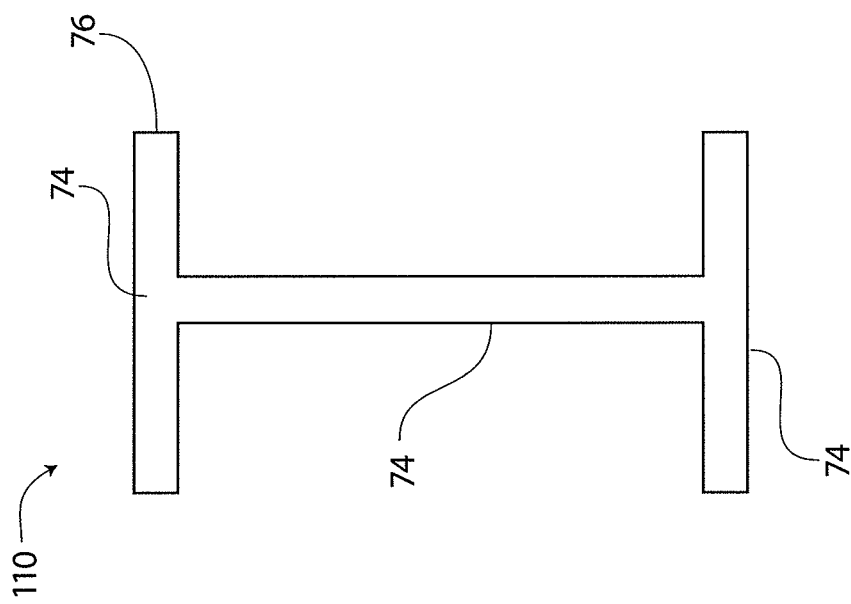
FIG. 6A is a front view of another integrated implant.

FIGS. 6A-B is a front view and perspective view, respectively, of another integrated implant. The hollow or open integrated implant 110 includes wall portions 74 and cutting edges 76. Although no delivery pin hole 78 is illustrated, the integrated implant 110 may include one or more delivery pin holes 78. Wall portions 74 may form an I-beam shape. The I-beam shape may be formed by three wall portions 74 forming a letter "I". In various embodiments, the integrated implant 110, in contrast to an I-beam configuration used in building construction, may not require right angles at the junction between the "I" wall portion 74 and the top and bottom wall portions 74. (See FIG. 14B)

The cutting edges 76 may be implemented on one or more of the wall portions 74. In various embodiments, each wall portion 74 may include a cutting edge 76. Each cutting edge 76 may be implemented as any of the cutting edges discussed with respect to FIGS. 4A-E. The thickness of the wall of wall portions 74 and 75 may be about 1 mm. In various embodiments, the thickness of wall portions 74 and 75 is in the range of about 0.5 mm to 5 mm. In various embodiments, the length of integrated implant 110 is in the range of about 10 mm to 70 mm. In various embodiments, the length of the integrated implant 110 is about 30 mm, 35 mm, 40 mm, 45 mm, 50 mm, 55 mm, 60 mm, 65 mm, and 70 mm.

FIGS. 7A-M are illustrations of cross-sectional geometries of exemplary integrated implants. Each of FIGS. 7A-M illustrate a geometry, a delivery pin hole and broaching edges.

Figure 7A:
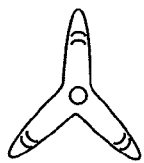
FIGS. 7A-M are illustrations of cross-sectional geometries of exemplary integrated implants.
Figure 7B:
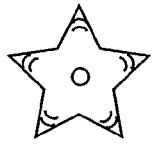

FIG. 7A illustrates a tri-legged integrated implant. The integrated implant of FIG. 7A includes three legs, which each leg having broaching edges towards the end of the leg. The integrated implant of FIG. 7A further includes a delivery pin hole at the center of the implant. FIG. 7B illustrates a star shaped integrated implant having a plurality of points, such as five points. Each point may include broaching edges, and a delivery pin hole may be located in the center of the star shaped integrated implant.

Figure 7C:
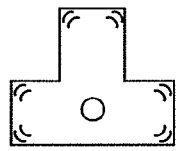
Figure 7D:
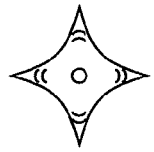

FIG. 7C illustrates a T-shaped integrated implant. Each corner of the T-shaped integrated implant may include broaching edges. A delivery pin hole may be positioned within the T-shaped integrated implant in a variety of positions, such as for example centered along the horizontal portion of the T-shape. FIG. 7D illustrates a kite shaped or diamond shaped integrated implant having four points. Each point may include broaching edges, and a delivery pin hole may be positioned in the center of the kite or diamond shaped integrated implant.

Figure 7E:
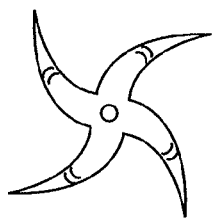
Figure 7F:
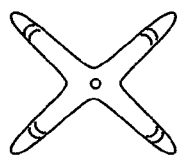

FIG. 7E illustrates a curved end four-pointed star-shaped integrated implant. The curved star-shaped integrated implant has four curved extensions, each of which includes a broaching edge. A delivery pin hole may be located in the center of the star. The edges may be less rounded or more rounded than the star shaped implant illustrated in FIG. 7E. FIG. 7F illustrates a straight end four-pointed star-shaped or X-shaped integrated implant. The straight star-shaped integrated implant has four straight extensions, each of which includes a broaching edge, and a delivery pin hole in the middle of the star.

Figure 7G:
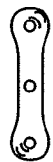
Figure 7H:
Figure 7I:
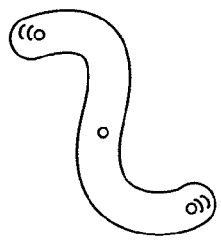

FIG. 7G illustrates a dumbbell shaped integrated implant. The integrated implant of FIG. 7G includes a delivery pin hole at the center and at each the two ends of the implant. Each end may also have broaching edges. FIG. 7H illustrates a bean shaped integrated implant. The bean shaped integrated implant includes a delivery pin hole at the implant center and broaching edges at each of the two ends of the integrated implant. FIG. 7I illustrates an S-shaped integrated implant having a delivery pin hole in the center and at each end. Broaching edges may be located at the integrated implant ends.

Figure 7J:
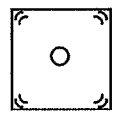
Figure 7K:
Figure 7L:
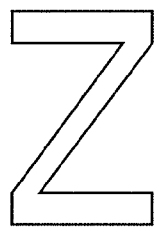
Figure 7M:
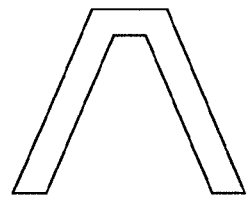

FIG. 7J illustrates a square shaped integrated implant. The square shaped implant includes broaching edges at each corner of the implant, and a delivery pin hole at the center of the square shape. FIG. 7K illustrates an oval shaped integrated implant having broaching edges at the narrow ends of the oval and a delivery pin hole at the center of the oval. FIG. 7L illustrates a Z-shape integrated implant. The integrated implant of FIG. 7L may include a delivery pin hole along the center vertical portion of the Z-shape as well as a delivery pin hole at one or more ends. The broaching edges may be positioned at each end as well. FIG. 7M illustrates a V-shape integrated implant. The integrated implant of FIG. 7M may include a delivery pin hole at the top of the inverted V-shape shown as well as a delivery pin hole at one or more ends. The broaching edges may be positioned on one or more of the two V-shape ends as well.

FIGS. 8A-8D are illustrations of an exemplary procedure for implanting the integrated implant of FIG. 1A. More detailed, anatomically-focused descriptions of particular implantation techniques of the integrated implant 20 in the SI-Joint are described with respect FIGS. 9-13B.

Figure 8A:
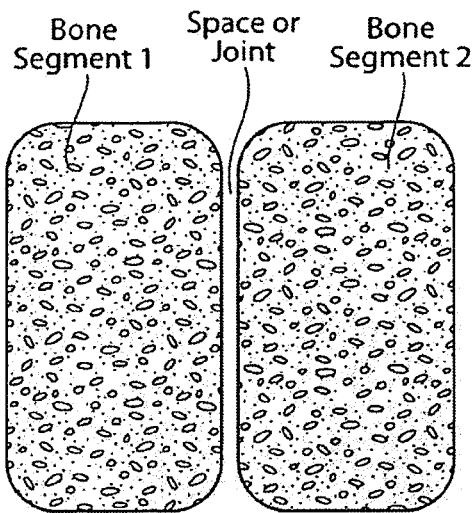
FIGS. 8A-8D are illustrations of an exemplary procedure for implanting the integrated implant of FIG. 1A.
Figure 8B:
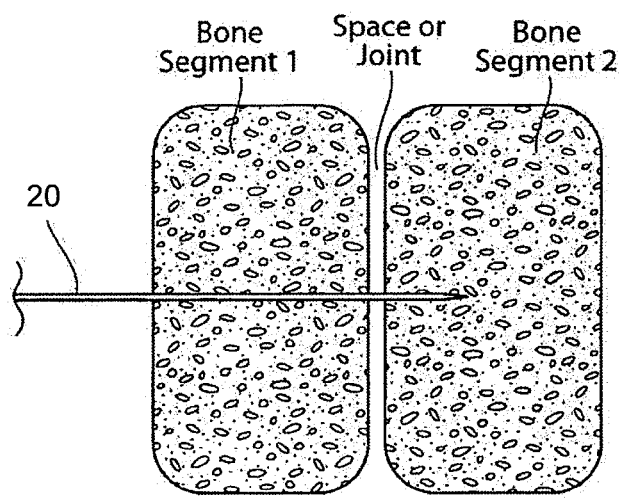

The physician identifies the bone segments or adjacent bone regions that are to be fixated or fused (arthrodesed) (see FIG. 8A). Aided by conventional visualization techniques, e.g., using X-ray image intensifiers such as a C-arms or fluoroscopes to produce a live image feed that is displayed on a TV screen, a delivery pin 26 is introduced by conventional means (see FIG. 8B) through the one adjacent bone segment or region (bone segment 1), through the intervening space or joint, and partially into the other adjacent bone segment or region (bone segment 2).

A cannulated drill bit 90 may be passed over the delivery pin 26 (see FIG. 8C), to form a pilot insertion path or bore 92 through the one adjacent bone segment or region, through the intervening space or joint, and partially into the other adjacent bone segment or region. A single drill bit or multiple drill bits 90 may be employed to drill through bone fragments or bone surfaces to create a pilot bore 92 of the desired size and configuration. When the pilot bore 92 is completed, the cannulated drill bit 90 is removed.

An integrated implant 20, which is triangular in the illustrated embodiment (see FIG. 8D), is tapped over the delivery pin 26 through the pilot bore 92. The integrated implant 20 cuts along the edges of the pilot bore 92 to form the desired profile to accommodate the geometry of the integrated implant 20 through the one adjacent bone segment or region, through the intervening space or joint, and partially into the other adjacent bone segment or region.

In various embodiments, integrated implant 20 may be positioned without forming a pilot insertion path or bore 92. Integrated implant 20 may be positioned by directly tapping the delivery rod until progress is prevented by the safety stop feature as described with respect to FIGS. 1A-2B.

In the case of integrated implant 50 shown in FIGS. 2A and 2B, the implant structure includes cutting broach 30 and cutting burr 38. The addition of cutting burr 38 allows for elimination of creating a pilot bore 92 in the bone with a separate cannulated drill bit 90. Rather, the pilot bore 92 is generated by cutting burr 38 as part of integrated implant 50. Hence, integrated implant 50 may be used to generate a pilot bore 92 at the same time the integrated implant is positioned through the one adjacent bone segment or region, through the intervening space or joint, and partially into the other adjacent bone segment or region. Integrated implant 50 may be simultaneously tapped into position while the pilot bore is being formed. (See FIG. 8D)

Figure 9:
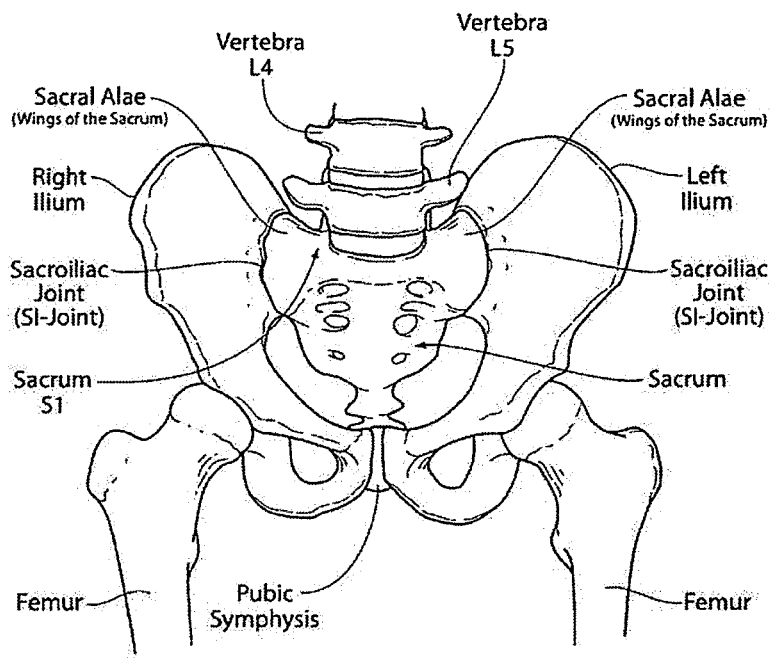
FIGS. 9-10 are, respectively, anterior and posterior anterior views of the human hip girdle comprising the sacrum and the hip bones (the right ilium, and the left ilium), the sacrum being connected with both hip bones at the sacroiliac joint (in shorthand, the SI-Joint).
Figure 10:
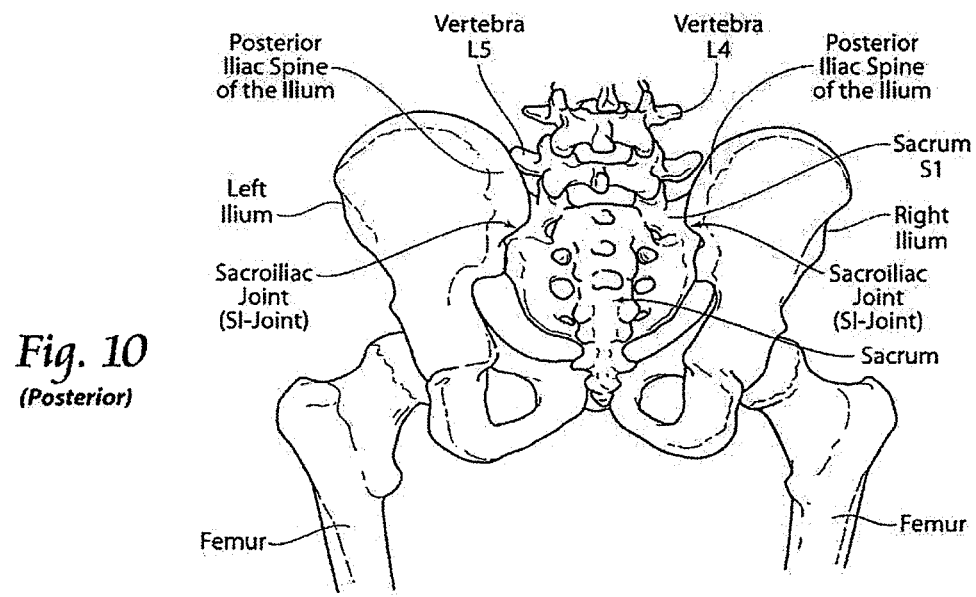

FIGS. 9-10 are, respectively, anterior and posterior anterior views of the human hip girdle comprising the sacrum and the hip bones (the right ilium, and the left ilium), the sacrum being connected with both hip bones at the sacroiliac joint (in shorthand, the SI-Joint). Elongated, stem-like integrated implant structures 20,50 like that shown in FIGS. 1A and 2A (and the alternative embodiments) make possible the fixation of the SI-Joint (shown in anterior and posterior views, respectively, in FIGS. 9 and 10) in a minimally invasive manner.

Integrated implant structures 20, 50 may be effectively implanted through the use of two alternative surgical approaches; namely, a lateral approach or a postero-lateral approach. Either procedure is desirably aided by conventional lateral and/or anterior-posterior (A-P) visualization techniques, e.g., using X-ray image intensifiers such as a C-arms or fluoroscopes to produce a live image feed that is displayed on a TV screen.

Figure 11:
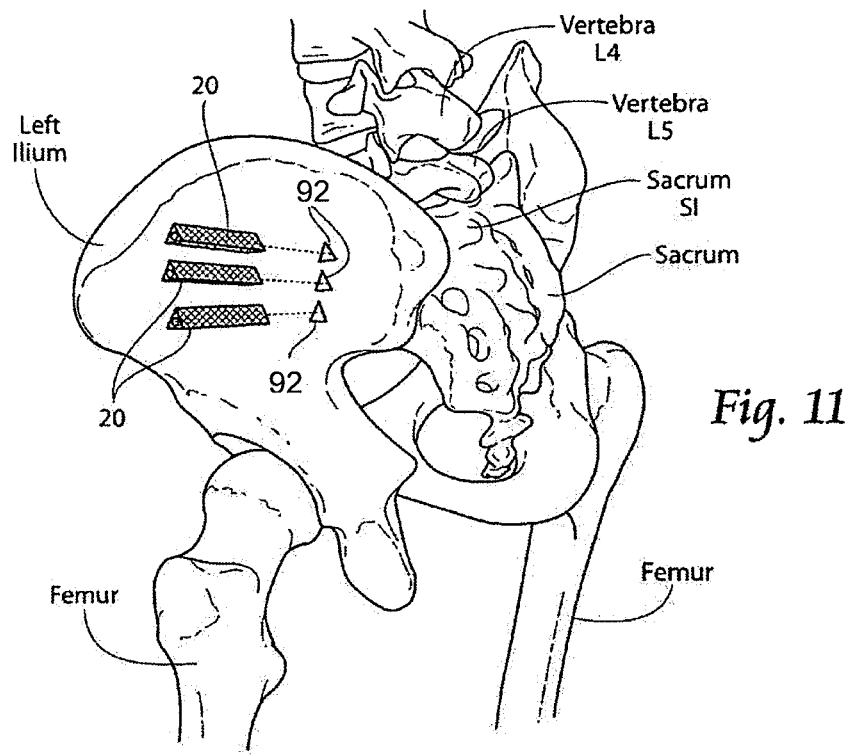
FIGS. 11-13B are anatomic views showing, respectively, in pre-implanted perspective, implanted perspective, implanted anterior view, and implanted cranio-caudal section view, the implantation of three implant structures for the fixation of the SI-Joint using a lateral approach through the ilium, the SI-Joint, and into the sacrum.
Figure 12:
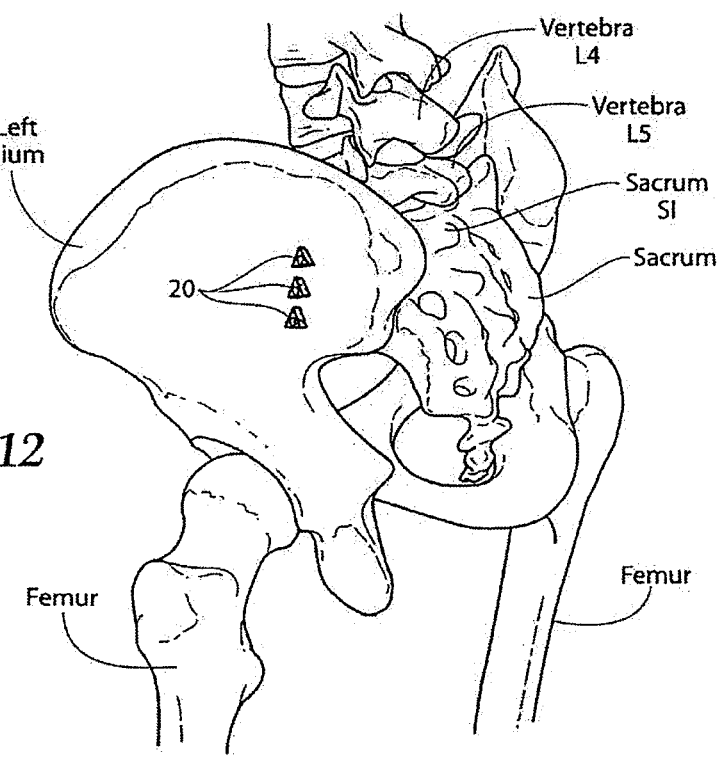
Figure 13A:
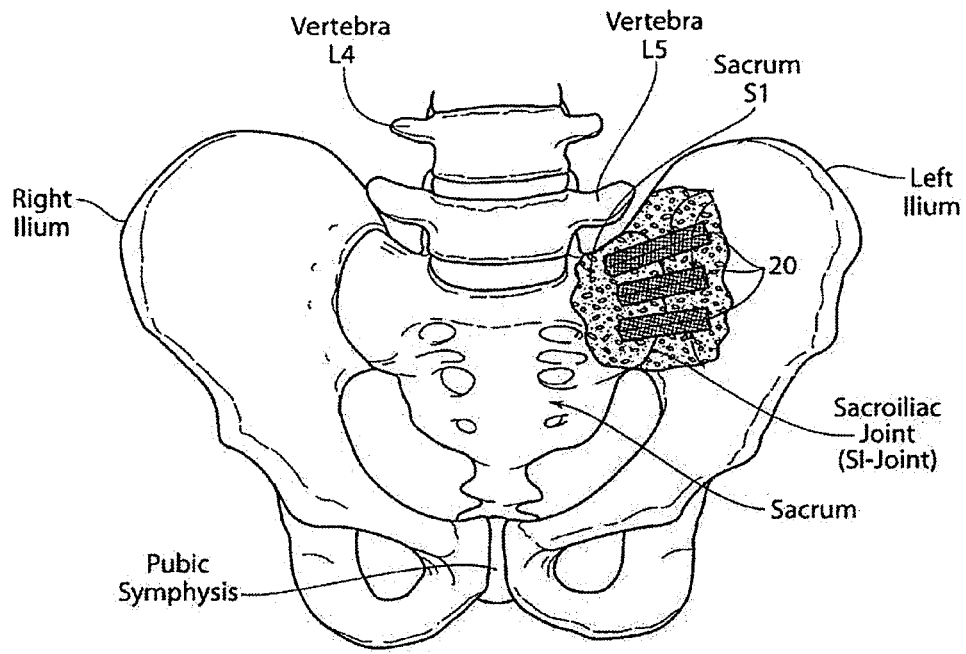
Figure 13B:
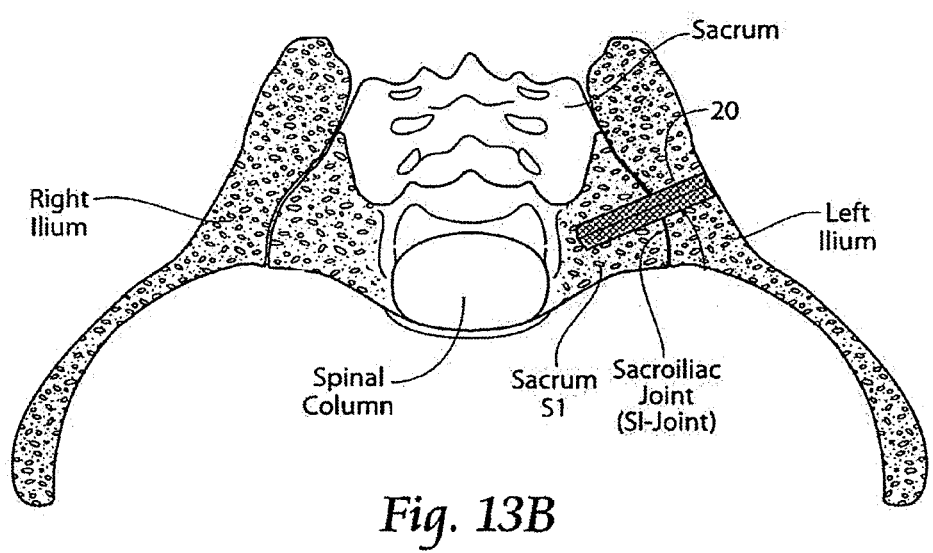

FIGS. 11-13B are anatomic views showing, respectively, in pre-implanted perspective, implanted perspective, implanted anterior view, and implanted cranio-caudal section view, the implantation of three implant structures for the fixation of the SI-Joint using a lateral approach. In one embodiment of a lateral approach (see FIGS. 11-13B), one or more integrated implant structures 20, 50 are introduced laterally through the ilium, the SI-Joint, and into the sacrum. This path and resulting placement of the integrated implant structures 20, 50 are best shown in FIGS. 12-13B. In the illustrated embodiment, three integrated implant structures 20, 50 are placed in this manner. Also in the illustrated embodiment, the integrated implant structures 20, 50 are triangular in cross section, but it should be appreciated that integrated implant structures of other cross sections as previously described may be used.

Before undertaking a lateral implantation procedure, the physician identifies the SI-Joint segments that are to be fixated or fused (arthrodesed) using, e.g., the Fortin finger test, thigh thrust, FABER, Gaenslen's, compression, distraction, and diagnostic SI joint injection.

Aided by lateral, inlet, and outlet C-arm views, and with the patient lying in a prone position (on their stomach), the physician aligns the greater sciatic notches using lateral visualization to provide a true lateral position. A 3 cm incision is made starting aligned with the posterior cortex of the sacral canal, followed by blunt-tissue separation to the ilium. From the lateral view, the delivery pin 26, a Steinmann Pin for example, with a pin sleeve (not shown), is started resting on the ilium at a position inferior to the sacrum end plate and just anterior to the sacral canal and at a shallow angle (e.g., 15° to 20° off the floor, as FIG. 13B shows). In the outlet view, the delivery pin 26 should be parallel to the sacrum end plate or angled slightly away from the sacrum end plate. In a lateral view, the delivery pin 26 should be posterior to the sacrum anterior wall. In the outlet, the delivery pin 26 should be superior to the sacral inferior foramen and lateral of mid-line. This corresponds generally to the sequence shown diagrammatically in FIGS. 8A-B. A soft tissue protector (not shown) or flexible sheath 22 is desirably slipped over the delivery pin 26 and thinly against the ilium before removing the pin sleeve. In the inlet view, the trajectory of the delivery pin 26 must no penetrate the anterior sacral cortex before the patient's sagittal midline.

Figure 8C:
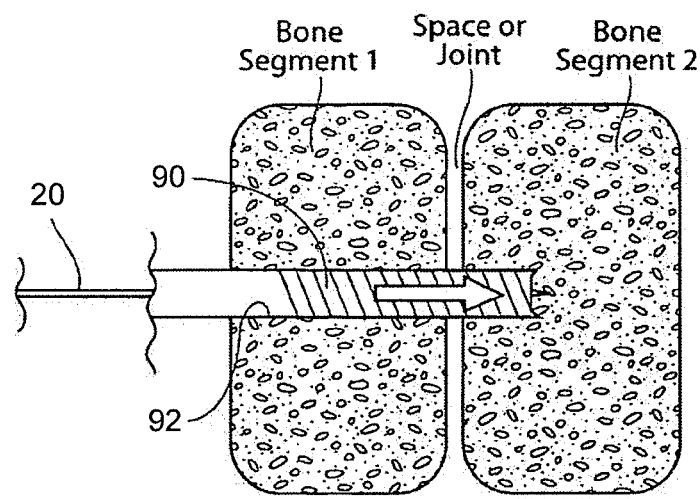
Figure 8D:
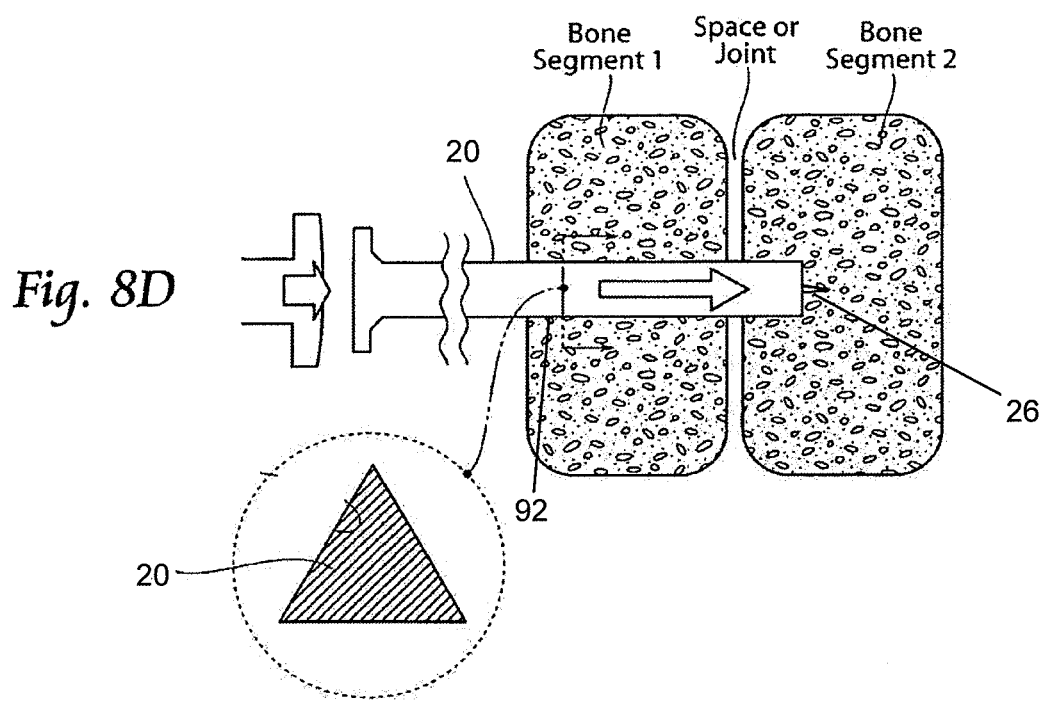

The pilot bore 92 may be drilled in the manner previously described over the delivery pin 26 (and through the soft tissue protector or flexible sheath), as illustrated in FIG. 8C. The pilot bore 92 may extend through the ilium, through the SI-Joint, and into the sacrum. The drill bit 90 is then removed.

The integrated implant 20 is tapped into the pilot bore 92 over the delivery pin 26 (and through the soft tissue protector or flexible sheath). The integrated implant 20 with cutting broach 30 eliminates an additional step that requires using a separate broach to create a broached bore with the desired profile for the integrated implant structure 20.

As shown in FIGS. 11 and 12, a triangular integrated implant 20 may be tapped through the soft tissue protector or flexible sheath over the delivery pin 26 through the ilium, across the SI-Joint, and into the sacrum, until the proximal end of the integrated implant 20 is flush against the lateral wall of the ilium (see also FIGS. 13A-B). In various embodiments, the delivery pin 26 and soft tissue protector or flexible sheath are withdrawn, leaving the integrated implant 20 residing in the broached passageway, flush with the lateral wall of the ilium (see FIGS. 13A-B). In other embodiments, the proximal end of the integrated implant 20 is left proud of the lateral wall of the ilium, such that it extends 1, 2, 3, 4, or 5 mm outside of the ilium. This ensures that the integrated implant 20 engages the hard cortical portion of the ilium rather than just the softer cancellous portion, through which it might migrate if there was no structural support from hard cortical bone. The hard cortical bone can also bear the loads or forces typically exerted on the bone by the integrated implant 20. In various embodiments, the delivery pin 26 may not be withdrawn but instead remains implanted with the integrated implant. In the illustrated embodiment, two additional integrated implants 20 are delivered in this manner, as FIG. 12 best shows.

In the case of integrated implant 50, the implant structure includes cutting broach 30 and cutting burr 38. The addition of cutting burr 38 allows for elimination of creating a pilot bore 92 in the bone with a separate drill. Rather, the pilot bore 92 is generated by cutting bore 38 as part of the insertion of integrated implant 50.

The integrated implants 20, 50 are sized according to the local anatomy. For the SI-Joint, representative integrated implants 20, 50 may range in size, depending upon the local anatomy, from about 30 mm to about 70 mm in length, and about a 7 mm inscribed diameter (i.e. a triangle having a height of about 10.5 mm and a base of about 12 mm). The morphology of the local structures can be generally understood by medical professionals using textbooks of human skeletal anatomy along with their knowledge of the site and its disease or injury. The physician is also able to ascertain the dimensions of the integrated implant 20, 50 based upon prior analysis of the morphology of the targeted bone using, for example, plain film x-ray, fluoroscopic x-ray, or MRI or CT scanning, as well as intraoperative sizing methods using provided instrumentation.

Figure 14D:
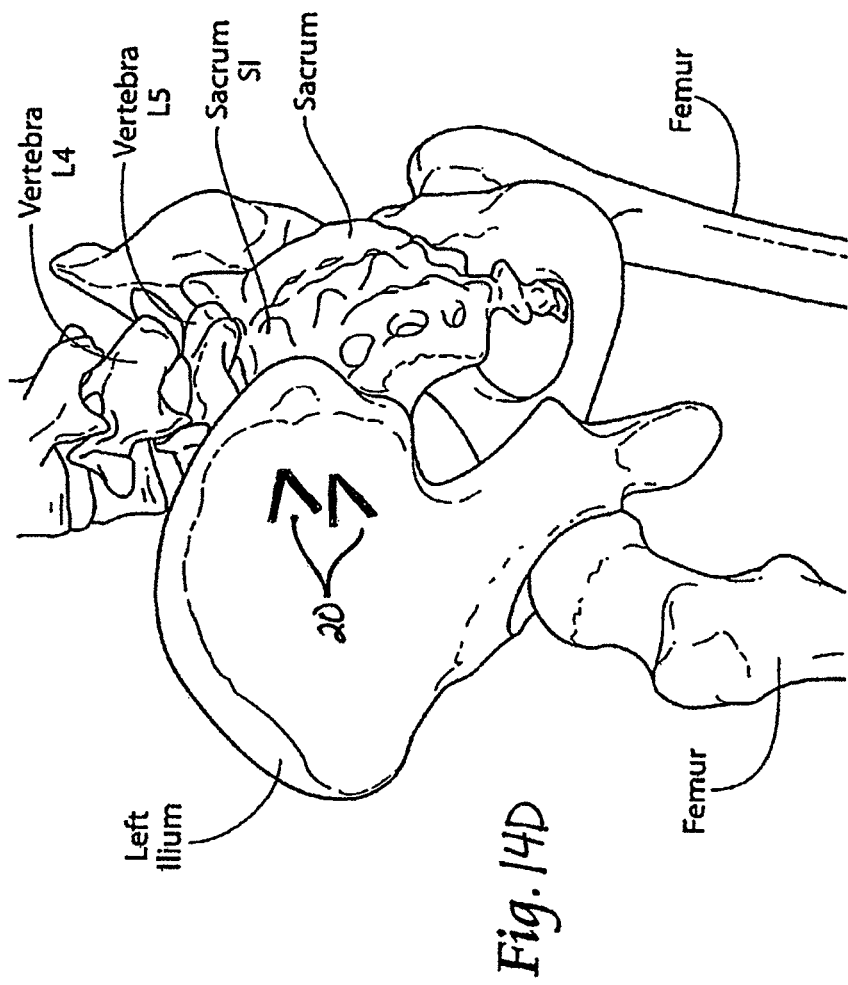

FIGS. 14A-D are anatomic views of implanted exemplary integrated implants. The number of integrated implants to use within a patient may vary. FIG. 14A illustrates two integrated implants 100 having a cross-sectional geometry resembling a bow-tie as shown in FIG. 5. The integrated implants of FIG. 14A are adjacent and are about the same size. In various embodiments, more or fewer implants may be used. Integrated implants 100 may be inserted into bone in a manner similar to that described with respect to FIGS. 11-12.

FIG. 14B illustrates two integrated implants 110 having a cross-sectional geometry resembling the shape of an I-beam as shown in FIGS. 6A-B. The integrated implants of FIG. 14B are adjacent and are about the same size. Integrated implants 110 may be inserted into bone in a manner similar to that described with respect to FIGS. 11-12.

FIG. 14C illustrates two integrated implants 20 having a cross-sectional geometry resembling a letter "Z" as shown in FIG. 7L. The integrated implants of FIG. 14C are adjacent and are about the same size. Integrated implants 20 may be inserted into bone in a manner similar to that described with respect to FIGS. 11-12.

FIG. 14D illustrates two integrated implants 20 having a cross-sectional geometry resembling a letter "V" as shown in FIG. 7M. The integrated implants of FIG. 14D are adjacent and are about the same size. Integrated implants 20 may be inserted into bone in a manner similar to that described with respect to FIGS. 11-12.

The integrated implant structures can obviate the need for autologous grafts, bone graft material, additional pedicle screws and/or rods, hollow modular anchorage screws, cannulated compression screws, cages, or fixation screws. Still, in the physician's discretion, bone graft material and other fixation instrumentation can be used in combination with the integrated implants 20.

The integrated implants 20, 50 make possible surgical techniques that are less invasive than traditional open surgery with no extensive soft tissue stripping and no disc removal. The assemblies make possible straightforward surgical approaches that complement the minimally invasive surgical techniques. The profile and design of the integrated implants 20 minimize rotation and micro-motion. Rigid integrated implants 20 made from titanium provide immediate post-op fusion stability. A bony in-growth region comprising a porous plasma spray coating with irregular surface supports stable bone fixation/fusion. The integrated implants 20 and surgical approaches make possible the placement of larger fusion surface areas designed to maximize post-surgical weight bearing capacity and provide a biomechanically rigorous implant designed specifically to stabilize the heavily loaded sacroiliac joint.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the examples described herein, but only by the plain meaning of the claim terms employed.

What is claimed is:

1. A bone fusion implant comprising:
   a core having a hollow structure formed by a multi-sided wall;
   a delivery pin hole within the core extending from a proximal end to a distal end of the core, the delivery pin hole configured to securely receive a delivery pin; and
   a plurality of cutting edges at a distal end of the multi-sided wall, the plurality of cutting edges configured to cut through bone; wherein the multi-sided wall comprises a plurality of interlocking wall sections, the wall sections configured to be implanted independently and interlocked after insertion into a patient.

2. The implant of claim 1, wherein a tapering distal end of the multi-sided wall forms a jagged cutting edge at a distal edge of the multi-sided wall.

3. The implant of claim 1, wherein the implant comprises a triangular cross-section.

4. The implant of claim 1, wherein the multi-sided wall is made of a metal.

5. The implant of claim 1, wherein the multi-sided wall has an outer surface that is porous.

6. The implant of claim 5, wherein the multi-sided wall has an outer surface that is coated with a biologic aid.

7. The implant of claim 6, wherein the biologic aid is hydroxyapatite.

8. The implant of claim 6, wherein the biologic aid is bone morphogenetic protein.

9. The implant of claim 8, wherein the bone morphogenetic protein is incorporated into a controlled release formulation.

10. The implant of claim 1, wherein the multi-sided wall has a plurality of fenestrations.

11. The implant of claim 1, wherein the plurality of cutting edges taper to points.

\* \* \* \* \*